(12) United States Patent
Cattaneo et al.

(10) Patent No.: US 10,709,588 B2
(45) Date of Patent: Jul. 14, 2020

(54) MEDICAL DEVICE AND SYSTEM HAVING SUCH A DEVICE

(71) Applicant: ACANDIS GMBH & CO. KG, Pforzheim (DE)

(72) Inventors: Giorgio Cattaneo, Karlsruhe (DE); Otto Baidinger, Pforzheim (DE)

(73) Assignee: ACANDIS GMBH & CO. KG, Pfinztal (DE)

( * ) Notice: Subject to any disclaimer, the term of this patent is extended or adjusted under 35 U.S.C. 154(b) by 0 days.

(21) Appl. No.: 15/351,746

(22) Filed: Nov. 15, 2016

(65) Prior Publication Data

US 2017/0112643 A1 Apr. 27, 2017

Related U.S. Application Data

(63) Continuation of application No. 13/818,664, filed as application No. PCT/EP2011/004309 on Aug. 26, 2011.

(30) Foreign Application Priority Data

Aug. 26, 2010 (DE) .......................... 10 2010 035 543

(51) Int. Cl.
*A61F 2/90* (2013.01)
*A61B 17/12* (2006.01)
(Continued)

(52) U.S. Cl.
CPC .......... *A61F 2/90* (2013.01); *A61B 17/12118* (2013.01); *A61F 2/852* (2013.01);
(Continued)

(58) Field of Classification Search
CPC ...... A61F 2002/821; A61F 2/852; A61F 2/90; A61F 2210/0076; A61F 2002/077;
(Continued)

(56) References Cited

U.S. PATENT DOCUMENTS 5,064,435 A 11/1991 Porter
5,330,500 A 7/1994 Song
(Continued)

FOREIGN PATENT DOCUMENTS

DE 10301600 7/2004
DE 69921481 2/2005
(Continued)

OTHER PUBLICATIONS

International Search Report for PCT/EP2011/004309, English translation attached to original, both completed by the European Patent Office dated Nov. 16, 2011, 7 pages.
(Continued)

*Primary Examiner* — Tan-Uyen T Ho
*Assistant Examiner* — Chima U Igboko
(74) *Attorney, Agent, or Firm* — Sterne, Kessler, Goldstein & Fox P.L.L.C.

(57) ABSTRACT

A medical device, having a body that is tubular at least in some sections. The body can be transferred from a compressed state into an expanded state and has a circumferential wall having at least one first lattice structure and one second lattice structure. The first lattice structure and the second lattice structure form separate layers of the circumferential wall, which are arranged coaxially one inside the other and connected to each other at least at points in such a way that the first lattice structure and the second lattice structure can be moved relative to each other at least in some sections. A system having such a device is also disclosed.

24 Claims, 16 Drawing Sheets

(51) Int. Cl.
*A61F 2/852* (2013.01)
*A61F 2/95* (2013.01)
*A61F 2/82* (2013.01)
*A61F 2/07* (2013.01)

(52) U.S. Cl.
CPC .......... *A61F 2/95* (2013.01); *A61F 2002/077* (2013.01); *A61F 2002/823* (2013.01); *A61F 2210/0076* (2013.01); *A61F 2230/0008* (2013.01); *A61F 2250/0015* (2013.01); *A61F 2250/0036* (2013.01); *A61F 2250/0063* (2013.01)

(58) Field of Classification Search
CPC ........ A61F 2250/0065; A61F 2250/006; A61F 2250/0023; A61F 2250/0015; A61F 2250/0036; A61F 2250/0063; A61F 2002/823; A61B 17/12113; A61B 17/12109; A61B 17/12118; A61B 2017/12127; A61B 2017/12168
USPC ........................................................ 623/1.16
See application file for complete search history.

(56) References Cited

U.S. PATENT DOCUMENTS

| | | | |
|---|---|---|---|
| 5,383,925 A * | 1/1995 | Schmitt | A61F 2/06 600/36 |
| 5,531,779 A | 7/1996 | Dahl et al. | |
| 5,645,559 A | 7/1997 | Hachtman et al. | |
| 5,718,159 A | 2/1998 | Thompson | |
| 5,928,228 A | 7/1999 | Kordis et al. | |
| 6,099,559 A | 8/2000 | Nolting | |
| 6,169,922 B1 | 1/2001 | Alferness et al. | |
| 6,331,188 B1 | 12/2001 | Lau | |
| 6,348,066 B1 | 2/2002 | Pinchuk et al. | |
| 6,445,983 B1 | 9/2002 | Dickson et al. | |
| 6,600,956 B2 | 7/2003 | Maschino et al. | |
| 6,685,736 B1 | 2/2004 | White et al. | |
| 6,709,455 B1 | 3/2004 | Chouinard | |
| 6,887,268 B2 | 5/2005 | Butaric et al. | |
| 6,934,583 B2 | 8/2005 | Weinberg et al. | |
| 7,060,089 B2 | 6/2006 | Ley et al. | |
| 7,108,716 B2 | 9/2006 | Burnside et al. | |
| 7,231,260 B2 | 6/2007 | Wallace et al. | |
| 7,588,597 B2 | 9/2009 | Frid | |
| 8,303,650 B2 | 11/2012 | Shokoohi | |
| 8,308,928 B2 | 11/2012 | Quandt et al. | |
| 8,801,768 B2 | 8/2014 | Karwa et al. | |
| 2001/0044647 A1 | 11/2001 | Pinchuk et al. | |
| 2003/0074039 A1 | 4/2003 | Puskas | |
| 2003/0149473 A1 * | 8/2003 | Chouinard | A61F 2/91 623/1.15 |
| 2004/0098095 A1 * | 5/2004 | Burnside | A61F 2/07 623/1.13 |
| 2004/0199243 A1 | 10/2004 | Yodfat | |
| 2005/0137680 A1 * | 6/2005 | Ortiz | A61F 2/90 623/1.16 |
| 2005/0278017 A1 | 12/2005 | Gregorich | |
| 2006/0058872 A1 | 3/2006 | Salahieh et al. | |
| 2006/0116752 A1 | 6/2006 | Norton | |
| 2007/0106359 A1 | 4/2007 | Schaer et al. | |
| 2007/0168019 A1 * | 7/2007 | Amplatz | A61F 2/07 623/1.18 |
| 2007/0198075 A1 | 7/2007 | Levy | |
| 2008/0262593 A1 | 10/2008 | Ryan et al. | |
| 2008/0262594 A1 | 10/2008 | Morris | |
| 2009/0024195 A1 | 1/2009 | Rezai et al. | |
| 2009/0088833 A1 | 4/2009 | Soetermans | |
| 2009/0127226 A1 | 5/2009 | Quandt et al. | |
| 2009/0248133 A1 | 10/2009 | Bloom et al. | |
| 2009/0270974 A1 * | 10/2009 | Berez | A61B 17/12118 623/1.17 |
| 2009/0312834 A1 * | 12/2009 | Wood | A61F 2/90 623/1.44 |
| 2009/0319029 A1 | 12/2009 | Evans et al. | |
| 2010/0049310 A1 | 2/2010 | Quandt et al. | |
| 2011/0046718 A1 | 2/2011 | Cattaneo et al. | |
| 2011/0093002 A1 * | 4/2011 | Rucker | A61F 2/90 606/198 |
| 2012/0277788 A1 | 11/2012 | Cattaneo | |
| 2012/0323309 A1 | 12/2012 | Cattaneo | |
| 2014/0058436 A1 | 2/2014 | Rosenbluth et al. | |

FOREIGN PATENT DOCUMENTS

| | | |
|---|---|---|
| DE | 102005018731 | 10/2006 |
| DE | 102006007231 | 8/2007 |
| DE | 60128588 | 2/2008 |
| DE | 102006039840 | 3/2008 |
| DE | 102007061931 | 6/2009 |
| DE | 102008010507 | 8/2009 |
| DE | 102009056450 | 6/2011 |
| DE | 102009060228 | 6/2011 |
| DE | 102009060280 | 6/2011 |
| EP | 0737452 | 10/1996 |
| EP | 1304135 | 4/2003 |
| EP | 1374799 | 1/2004 |
| EP | 1645246 | 4/2006 |
| EP | 2014239 A2 | 1/2009 |
| WO | WO 98/29057 A1 | 7/1998 |
| WO | WO 99/49812 A2 | 10/1999 |
| WO | WO 2005110528 | 11/2005 |
| WO | WO 2007039587 | 4/2007 |
| WO | WO 2007105060 | 9/2007 |
| WO | WO 2008009434 | 1/2008 |
| WO | WO 2008/062414 | 5/2008 |
| WO | WO 2008094789 | 8/2008 |
| WO | WO 2009/002330 A1 | 12/2008 |
| WO | WO 2011049823 | 4/2011 |

OTHER PUBLICATIONS

Final Office Action for U.S. Appl. No. 13/818,663, dated Jan. 9, 2015, 8 pages.
Non-Final Office Action for U.S. Appl. No. 13/818,663, dated Sep. 9, 2014, 16 pages.

* cited by examiner

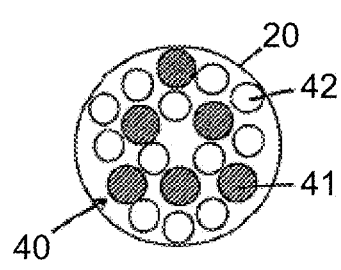
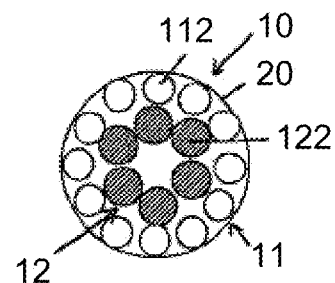
FIG. 6A
(Prior art)
FIG. 6B
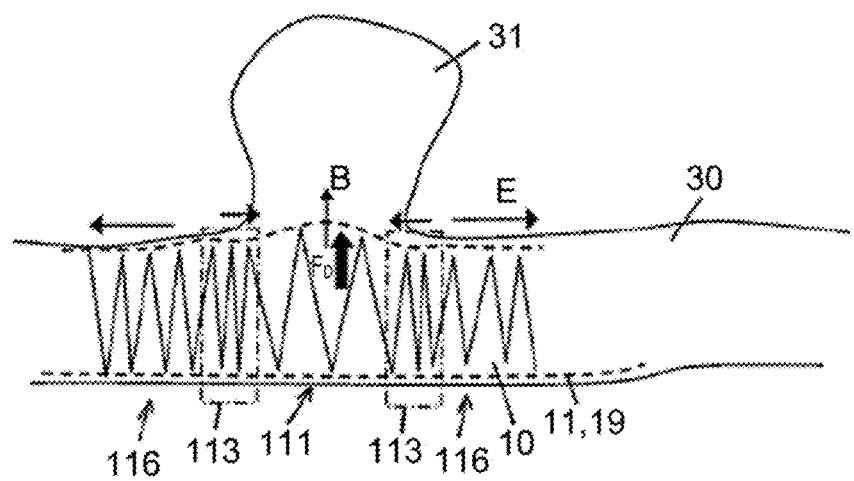
FIG. 7

MEDICAL DEVICE AND SYSTEM HAVING SUCH A DEVICE

CROSS-REFERENCE TO RELATED APPLICATIONS

This application is a continuation of U.S. application Ser. No. 13/818,664, having a 371(c) date of May 3, 2013, which is the U.S. national phase of International Application No. PCT/EP2011/004309, filed Aug. 26, 2011, which claims priority to German Patent Application No. 10 2010 035 543.7, filed Aug. 26, 2010, the disclosures of which are incorporated in their entirety by reference herein.

BACKGROUND

Field

The invention relates to a medical device having a body which is tubular at least in some sections, can be transferred from a compressed state to an expanded state and has a circumferential wall with at least a first lattice structure and a second lattice structure. The invention further relates to a system having such a device.

Discussion of Related Art

DE 601 28 588 T2 discloses a stent whose tubular structure is formed by a plurality of layers. The individual layers each comprise a wire braid, the wire braids being interwoven. The wire braids of the individual layers are therefore in each case woven with the wire braid of an adjacent layer and thus form a connection between the layers that covers a large surface area. This results overall in a relatively complex braided structure of the wall of the stent.

The complex braided structure increases the fine mesh of the known stent, and this is intended to have advantages in the treatment of aneurysms. Specifically, the stent is used to impede the flow of blood into an aneurysm, by means of the stent being placed in a blood vessel in the area of an aneurysm. For this purpose, the stent is guided in a conventional manner known per se to the treatment site via a delivery system. The stent lies in a compressed state inside the delivery system. In other words, the stent has a minimal cross-sectional diameter in the delivery system. In the area of the treatment site, the stent is released from the delivery system. The stent is in particular expanded or widened at the treatment site, such that the stent bears on the vessel wall of the blood vessel. The expansion can take place automatically (self-expandable stents) or with the aid of a balloon of the delivery system (balloon-expandable stents).

The known stent has disadvantages. The complex braided structure, in which the individual wire elements are interwoven over a plurality of layers of the walls, means that, when the known stent is in the compressed state, the individual wires inside the delivery system are in an arrangement that requires a large amount of space. This arrangement is seen particularly in the cross section of the compressed known stent, which is shown by way of example in FIG. 6a. Here, the first wires 41 of a first braid layer have a larger cross-sectional diameter than the second wires 42 of a second braid layer. The first wires 41 of the first braid layer are interwoven with the second wires 42 of the second braid layer. In the compressed state, this results in the bulky arrangement as per FIG. 6a. Relatively large free spaces between the first and second wires 41, 42 remain unused, such that the known stent, in the compressed state, has a relatively large overall cross-sectional diameter. This also influences the minimum possible cross-sectional diameter for the delivery system. Delivery of the known stent into quite small vessels is thus made more difficult.

As a result of the interweaving of the individual layers, the flexibility of the known stent is also adversely affected. In particular, the interwoven wires become blocked on each other, such that the known stent has a comparatively high degree of stiffness or low flexibility.

In general, aneurysms in blood vessels are affected by various physical phenomena that can lead to an enlargement or even a rupture of the aneurysm. These physical phenomena, arising from the physiology of the cardiovascular system, comprise, on the one hand, the transfer of the blood pressure into the aneurysm and, on the other hand, shear stresses which are caused by a flow of blood inside the aneurysm, and also local loads which act on the aneurysm wall or aneurysm neck and are caused when individual areas of the aneurysm are attacked directly by the blood flow.

Aneurysms mostly form in arteries, i.e. blood vessels leading away from the heart. On account of the pulsating pump action of the heart, the blood flow in arteries is subject to intense fluctuations of pressure. The maximum pressure peaks in the arterial system occur in the ejection phase of the heart, the systole. A pressure minimum is reached in the diastole, the filling phase of the heart chambers. The level of the local pressure within defined sections of the vessels is determined by, among other things, the compliance, i.e. the elasticity, of the vessel wall. The pressure fluctuations in the vessel are transferred through the aneurysm neck into the aneurysm. If untreated, the pressure inside the blood vessel is transferred almost completely into the aneurysm, which leads to increased loading of the already weakened aneurysm wall. There is a danger of the aneurysm rupturing. The flow of blood from the blood vessel into the aneurysm is impeded by the use of known stents, for example the aforementioned stent according to DE 601 28 588 T2. A through-flow resistance is thus created which reduces the velocity of the flow of the blood into the aneurysm. Therefore, during the systole, the pressure inside the aneurysm rises more slowly and to a lesser degree than inside the blood vessel. In other words, the transfer of pressure from the blood vessel into the aneurysm through the meshes of the stent is delayed and incomplete. FIG. 1c shows an example of the pressure profile of the blood pressure in the blood vessel (solid line) and the pressure curve of the blood pressure inside the aneurysm (broken line).

It is known from practice that, some hours or days after an aneurysm has been treated with known stents that impede the transfer of pressure into the aneurysm, fissures can appear in the aneurysm wall and lead to bleeding. In the treatment of aneurysms with the known stents, there is therefore still the danger of the aneurysm rupturing.

It is assumed that, when the aneurysm is covered by known stents that influence the blood pressure in the aneurysm, the cells of the aneurysm wall, including muscle cells in the area of the muscle layer (tunica media) of the vessel wall, degenerate as a result of the diminishing load. In other words, the cells of the aneurysm wall are used to the high pressure load. When the high pressure load is lost, degenerative processes can set in, as a result of which the mechanical properties of the vessel wall may undergo negative changes. The danger of a rupture of the vessel wall in the aneurysm region thus increases.

The blood flow inside an aneurysm is subject to a further physical phenomenon. As the blood in the blood vessel flows past the aneurysm neck, shear forces act at the interface between the blood in the blood vessel and the blood inside the aneurysm. The resulting shear stresses cause eddying of the blood inside the aneurysm. A flow eddy thus forms in the aneurysm. The eddy formation in the aneurysm prevents blood clotting inside the aneurysm. In particular, the eddy formation prevents areas of stasis from developing, which are seen as a precondition for agglomeration in the form of so-called rouleaux formation. The expression rouleaux formation, or pseudoagglutination, designates the reversible formation of chain-like stacks of red blood cells. With regard to the aforementioned degeneration of cells of the aneurysm wall, the obstruction of a tangential blood flow, which on account of shear stresses leads to an eddying of the blood flow inside the aneurysm, is regarded as disadvantageous. Up to a certain point, however, reduction of the shear stress is necessary to ensure that the blood can clot. However, if the reduction is too great, thrombus development takes place too rapidly. The fresh clot developing as a result of the blood stasis rapidly increases in volume, which can lead to fissures in the aneurysm wall.

Aneurysms in curved blood vessel sections have a further peculiarity in terms of the way they are influenced by the blood flow in the blood vessel. The curved shape of the vessel causes the blood in the blood vessel to be deflected in a curved trajectory. When an aneurysm develops at the apex of the curve, a flow component of the blood flow arises which is oriented substantially directly into the aneurysm, in particular onto the aneurysm neck. The blood from the blood vessel thus flows directly into the aneurysm. As soon as the inflowing blood strikes the aneurysm wall, particularly in the aneurysm head, the blood flow is deflected, as a result of which the kinetic flow energy of the blood is converted into a local pressure that locally stresses the aneurysm wall. The local inflow, and the local pressure resulting from the latter, can, in conjunction with the physiological pressure wave triggered by the systole and the diastole, be the cause of the development of the aneurysm. A reduction of the pressure wave can be positive in order to prevent the aneurysm growing any further, or even in order to achieve shrinkage of the aneurysm. On the other hand, the reduction can have a disadvantageous effect on the degeneration of the cells of the aneurysm wall.

By means of known stents that cover the aneurysm neck, the local pressure caused by the direct inflow of blood into the aneurysm is reduced or avoided, since the blood flow through the stent placed in the vessel is deflected into the predetermined curved trajectory. The fraction of the flow component routed directly into the aneurysm is thus reduced. At the same time, the known stents avoid the transfer of a pressure wave into the aneurysm, as a result of which the degeneration of the cells of the aneurysm wall is promoted.

Another possible way of avoiding direct flow onto an aneurysm is to influence the vessel curvature. For example, the radius of curvature of the vessel in the area of the aneurysm can be reduced by a suitable stent. A precondition for this is a stent structure that has sufficient stiffness or radial strength to ensure that the stent structure forces the blood vessel into a more elongate and less curved shape.

In practice, the above-described medical requirements concerning the treatment of aneurysms are satisfied by a number of different technical approaches. On the one hand, it is assumed that a very fine mesh, i.e. the smallest possible mesh size, of an aneurysm stent permits efficient treatment. The very fine mesh is usually obtained using a large number of wires. In order to achieve suitable crimpability, such that the aneurysm stent can be inserted into small blood vessels, the individual wires have a comparatively small cross-sectional diameter. Therefore, stents of this kind develop a comparatively low radial force. This means that stents of this kind do not permit any influence of the curvature of a blood vessel. Moreover, stents with a low radial force have low stability, which results in the danger of the stent moving away from its original position inside the blood vessel on account of the blood flow or the pulsation. There is therefore the danger of dislocation of the stent. In particular, cases are known from practice in which the inserted stents have migrated out of the blood vessel into the aneurysm and have caused further damage there. On account of the comparatively low radial force, stents of this kind also have a relatively small restoring force. Frictional forces between the stent and the vessel wall can mean that it is not possible to ensure an adaptation of the cross-sectional diameter of the stent to the cross-sectional diameter of the blood vessel, particularly under the influence of the systole and diastole. With large braiding angles, the lattice structure can easily squash together. As a result, the cells become smaller and the lattice structure becomes tighter. The permeability decreases, and the through-flow resistance increases, which can impair the flow conditions and can lead to occlusion of side branches of the vessels.

In the known stents, the comparatively fine mesh is also achieved through a large braiding angle. A large braiding angle also increases the foreshortening. Foreshortening is understood as a phenomenon in which the lattice structure of the stent shortens in the axial direction during the expansion, i.e. during the transfer from the compressed state to the expanded state. A large braiding angle causes a quite considerable shortening of the stent during the expansion. The positioning of such stents is made more difficult. There is the danger of the stent being wrongly positioned. The effect of the foreshortening is also seen in connection with the change of cross section of the blood vessel during the systole and diastole. Even with comparatively small changes of diameter, the stent with a large braiding angle can experience considerable lengthening or shortening. This also causes a change in the cell configuration and in the mesh size of the stent. The reproducibility of the treatment is thus made more difficult. By means of a large braiding angle, a high degree of flexibility is made available in the known stent. However, with flexible stents of this kind, the elongation of a curved blood vessel in order to reduce the impulse on the aneurysm wall is not possible.

A further disadvantage of stents known from practice is that the stents narrow at least in some sections during elongation. Such an elongation of the stent in the axial direction can be caused by the sequence of systole and diastole. During the systole, the vessel diameter is widened depending on the vessel compliance. Moreover, an axial elongation of the blood vessel takes place at the same time. The axial ends of a stent which is positioned inside the blood vessel, and which bears on the vessel wall, move away from each other during the elongation of the vessel. According to the foreshortening effect, the elongation of the stent causes at least in some sections a reduction of the stent diameter. The stent structure can then lift away from the aneurysm or from the aneurysm neck, as a result of which the effect of influencing the flow is reduced. Moreover, a narrowing of the stent diameter, triggered by an elongation of the stent, can cause the contact between stent and vessel wall to be reduced, with the resulting danger of dislocation of the stent.

The object of the invention is to make available a medical device which permits efficient treatment of aneurysms and has improved crimpability. In particular, the device is intended to prevent a postoperative rupture of the aneurysm or a postoperative weakening of the aneurysm wall. It is also the object of the invention to make available a system having such a device.

According to the invention, a device and system are disclosed.

The invention is based on the concept of making available a medical device, comprising a body which is tubular at least in some sections, can be transferred from a compressed state to an expanded state and has a circumferential wall with at least a first lattice structure and a second lattice structure. The first lattice structure and the second lattice structure form separate layers of the circumferential wall. The separate layers of the circumferential wall are arranged coaxially one inside the other. Moreover, the separate layers of the circumferential wall are connected to each other at least at points, in such a way that the first lattice structure and the second lattice structure are movable relative to each other at least in some sections.

According to the invention, the first lattice structure and the second lattice structure form separate layers of the circumferential wall. Therefore, the lattice structures are not connected to each other over a large surface area, as they are in the prior art. Instead, the connection between the lattice structures is punctiform, such that a relative movement is permitted between the layers or lattice structures.

Punctiform connection means that the area of the two lattice structures where they are arranged loosely on each other is greater in terms of surface area than the at least one connection area or the punctiform connection areas between the two lattice structures, in such a way that a relative movement is possible between the two lattice structures. The at least one connection area or the punctiform connection areas do not form a continuous lattice structure. Instead, the connection area is locally limited. For example, the connection area can in each case comprise individual cells or meshes of the two lattice structures in the area of which the mechanical connection exists. The punctiform connection area can be limited to at most 4 cells or meshes of the first and/or second lattice structure, wherein either 4 or fewer cells of the first lattice structure are connected to any desired number of cells, in particular to more than 4 cells, of the second lattice structure. The same applies conversely for the second lattice structure. It is also possible that both lattice structures are connected to each other in the area of at most 4 cells. The connection with 3 or 2 cells is disclosed explicitly. The punctiform connection can also comprise, for example, the connection of individual lattice elements of the two lattice structures, in particular lattice filaments made of plastic or metal, for example lattice wires and/or strands composed of several filaments, or wires, which can be twisted together or parallel alongside each other, i.e. not twisted together.

A punctiform connection is therefore understood as a connection limited to a partial area or a partial surface of the lattice structure, wherein in particular the ratio between the surface area of the connected lattice structures and the surface area of the free lattice structures is such that the lattice structures can move relative to each other in the free area, in particular can move relative to each other unimpeded. The surface area of the connected lattice structures is smaller than the surface area of the free lattice structures. The at least one punctiform connection can be arranged within the lattice structure. The punctiform connection has an areal extent (one or more connection points) or a linear extent (one or more connection lines) and is surrounded on all sides, or at least on two sides, particularly in the linear extent, by lattice structures arranged loosely on each other.

The punctiform connection can thus comprise at least one connection point, in particular several individual connection points each with an areal extent and/or at least one connection line, in particular several individual connection lines. A connection line can be formed from several individual connection points arranged in a row, in particular in the circumferential direction. The term connection point is not to be understood in the strict mathematical sense.

The punctiform connection can be arranged in the edge area, in particular at the edge of a lattice structure. The edge area as a whole can form the punctiform connection. The edge area forms an outer area which is arranged in the axial direction of the device and which is arranged at least outside the first intersection or the first cell segment of the lattice structure. The outer area can, for example, be the loop area of a braided stent. In a retractable braid with an obliquely tapering tip, as is described in DE 10 2009 056 450 or DE 10 2009 056 450, the content of each of which is fully incorporated by reference into this application, the area from the obliquely tapering tip to the in cross section cylindrically closed jacket area forms the edge area in which the lattice structures are connected. It is also possible to connect the lattice structures only at the oblique edge of the tip, for example by twisting the wires together.

If the punctiform connection is arranged at the edge of a lattice structure, the edge forms a limit of the connection. The other sides of the connection adjoin lattice structures arranged loosely on each other. Both lattice structures can each be connected at the edge, or one lattice structure at the edge and the other lattice structure away from the edge, for example in the middle area. This applies both to the first and also the second lattice structure.

It is also possible that the at least one punctiform connection is arranged outside the lattice structure, for example by connection strands or filaments or wires that extend over the lattice structures and are connected outside the lattice structures.

The punctiform connection can have different geometric shapes. For example, the shape of the connection can correspond to the shape of a cell or of several contiguous cells. Generally, the punctiform connection can be formed from individual subconnections, which for their part represent punctiform connections, for example in the form of individual wires or strands connected to each other at points. The higher-order punctiform connection is at least partially surrounded by lattice structures arranged loosely on each other, in such a way that, in the unconnected area of the lattice structures, a relative movement of the lattice structures is possible. This applies both to areal and also to linear punctiform connections.

The linear connection can extend in the circumferential direction and/or in the longitudinal direction and/or obliquely with respect to the longitudinal axis of the device. It preferably extends only in the circumferential direction or only in the longitudinal direction.

The length of the linear connection is at most 30%, in particular at most 25%, in particular at most 20%, in particular at most 15%, in particular at most 10%, in particular at most 5%, in particular at most 4%, in particular at most 3%, in particular at most 2%, in particular at most 1% of the total length of the device in the longitudinal direction or of the circumference of the device.

It is possible that the punctiform connection is arranged at the edge or even outside of the two lattice structures. For example, the two lattice structures can be connected by a common strand or guide wire by which the device can be actuated or can be moved in a delivery system. In this case, the two lattice structures are arranged loosely on each other across the entire surface area of the device and are fixed only at the axial end, where the two lattice structures are connected to the strand or to the guide wire.

The two layers or lattice structures are arranged coaxially one inside the other. This has the effect that the tubular body, in a compressed state, has a smaller cross-sectional diameter than in the prior art. Specifically, the invention provides for a regular arrangement of the individual wires or webs of the lattice structure, as a result of which the number of unused free spaces between the individual wires or webs is reduced. The crimpability or compressibility of the tubular body is thus increased.

By virtue of the double-walled structure, or the multi-layered design of the circumferential wall composed of mutually movable layers, it is possible to cover different application possibilities. Thus, in the device according to the invention, a division of functions can be provided in which one of the lattice structures has, for example, a carrying or supporting function, and the other or a further lattice structure has the function of influencing the flow in the area of an aneurysm.

The lattice structures or separate layers are connected to each other at points. The punctiform connection between the lattice structures ensures that the lattice structures substantially maintain their position relative to each other. In particular, the lattice structures maintain their relative position independently of a compressed or expanded state. Parts or sections of the lattice structures are able to move relative to each other. However, complete displacement of the two lattice structures relative to each other is prevented by the punctiform connection. In this way, the risk of dislocation of the medical device is minimized.

In a preferred embodiment of the medical device according to the invention, the first lattice structure and/or the second lattice structure is formed in each case from interwoven wires. Preferably, both lattice structures, or generally the lattice structures of the circumferential wall, each have a wire braid. The individual wire braids or lattice structures are therefore advantageously formed from several wires which extend in a spiral shape about a longitudinal axis of the tubular body. Wire spirals are provided that run in opposite directions and are interwoven. The individual layers of the circumferential wall are therefore formed by wire braids or interwoven wires or bands. However, the interweaving is present exclusively within an individual layer. The individual layers are interconnected at points, such that a relative movement between the layers is permitted.

It will be noted in this connection that the application does not only disclose and claim lattice structures that comprise a wire braid. Instead, the invention also includes lattice structures that are formed on the basis of lattice webs. Lattice structures of this kind can be produced, for example, by laser cutting or chemical vapor deposition.

In the context of the invention, provision is also made that each individual wire element of a lattice structure or of a layer comprises a single site at which the wire or the wires is or are connected to a wire or to wires of an adjacent layer. This has the effect that a punctiform connection exists between the layers.

The first lattice structure can have a proximal end, which is connected to a proximal end of the second lattice structure in such a way that distal ends of the first and second lattice structures arranged opposite the proximal ends are movable relative to each other. This embodiment goes back to the idea of interconnecting the lattice structures of the separate layers at in each case an axial end, in particular at the proximal ends. Thus, the entire lattice structure is movable between these. By contrast, the distal ends of the first and second lattice structures are arranged free, such that the distal ends of the lattice structure are movable relative to each other. The relative mobility of the lattice structures at least in some sections has the particular advantage of permitting a division of functions. In particular, the first and second lattice structures can have different geometries, such that different functions can be performed by the first and second lattice structures. The connection of the proximal ends of the lattice structures to each other is particularly advantageous, since the area where the lattice structures are movable relative to each other is quite large. In this way, different properties of the lattice structures can be combined across a relatively large area or the entire area of the tubular body. As an alternative to the connection of the proximal ends of the lattice structures, it is also possible that the distal ends of the first and second lattice structures are connected to each other. Moreover, the first and second lattice structures can be connected to each other at points in a middle area of the tubular body. The free ends of the lattice structures at the distal and/or proximal end of the device have the effect that the two lattice structures can shorten independently of each other during the expansion in the vessel (foreshortening), for example if the two lattice structures have different braiding angles.

It generally applies that a division of functions of the two structures is permitted by the only punctiform connection of the lattice structures.

According to another preferred embodiment, the first lattice structure and the second lattice structure, in a production state, have braiding angles that are the same at least in some sections or different from one another. Different braiding angles between the first lattice structure and the second lattice structure, or between the separate layers of the tubular body, have the effect that the lattice structures shorten to different extents during the expansion of the tubular body. Even in the event of a change of cross section of the hollow organ of the body in which the medical device is inserted, the lattice structures with different braiding angles behave differently. The different shortening of the lattice structures can be used advantageously for precise positioning of the medical device. For example, the second lattice structure can be designed in such a way that the effect of the foreshortening is reduced. The second lattice structure can therefore be positioned relatively exactly. Since the first lattice structure is connected to the second lattice structure at points, a precise positioning of the second lattice structure at the same time permits a relatively precise positioning of the first lattice structure or generally of the tubular body.

Preferably, the braiding angle of the first lattice structure and/or of the second lattice structure is at most 70°, in particular at most 65°, in particular at most 60°, in particular at most 59°, in particular at most 57°, in particular at most 55°, in particular at most 52°, in particular at most 50°. Such a braiding angle on the one hand ensures a sufficient flexibility of the lattice structures. On the other hand, such a braiding angle limits the foreshortening effect. Moreover, squashing together is reduced, such that the predetermined through-flow resistance is not impaired.

In a radially expanded state of the tubular body, a gap can be formed at least in some sections between the first lattice structure and the second lattice structure. Particularly in conjunction with different braiding angles for the first lattice structure and the second lattice structure, this ensures that, in the event of a change of the cross section or length of the hollow organ of the body in which the medical device is arranged, the two lattice structures lift away from each other. In this way, a gap is formed between the lattice structures, in particular an annular gap.

For example, the gap can be produced if the outer, second lattice structure or the outer net has, in the longitudinal direction, two spaced-apart, punctiform connections to the inner lattice structure, for example two connection lines extending in the circumferential direction, or individual connection points along two lines extending in the circumferential direction. The connection lines can be arranged at the axial ends of the lattice structure or can be offset axially inward from one or both ends. The two lattice structures have different braiding angles. The outer, second lattice structure has a smaller braiding angle and, therefore, a smaller foreshortening than the inner, first lattice structure. In the expanded state, the inner lattice structure is shortened to a greater extent than the outer lattice structure. This leads to an outward bulging of the second lattice structure and, therefore, to a gap between the two lattice structures. The difference in braiding angle can be at least 1°, in particular at least 2°, at least 3°, at least 4°, at least 5°, at least 10°, at least 15°, at least 20°, at least 25°, at least 30°. The upper limit for the range of the difference in braiding angle is at most 30°, in particular at most 25°, at most 20°, at most 15°, at most 10°, at most 5°, at most 4°, at most 3°, at most 2°, at most 1°. The aforementioned upper and lower limits can be combined with one another.

Generally, the bulge can occur between individual, axially spaced apart connection points, in particular between pairs of axially spaced apart connection points. It is possible to provide two longitudinally spaced apart connection lines composed of several connection points arranged in series in the circumferential direction. It is also possible to provide more than two such connection lines, between each of which a bulge is formed, such that several bulges are arranged in succession.

Flow eddies, which form a kind of cushion, develop in the gap between the lattice structures. The cushion leads to a desired loss of energy, such that the flow velocity is slowed down. The shear stresses in the main vessel thus act initially in the gap and generate the eddy there. The shear stresses transferred from the gap into the aneurysm via the wall of the net, or of the outer lattice structure, are thereby reduced. Clotting is promoted in the aneurysm. Moreover, the local pressure loads acting on the aneurysm wall and caused by the inflow of blood into the aneurysm are reduced.

Preferably, the first lattice structure and the second lattice structure each have closed meshes. The size of the meshes of the first lattice structure is advantageously different than the size of the meshes of the second lattice structure. In particular, the first lattice structure can have a smaller mesh size than the second lattice structure. In other words, the first lattice structure preferably has a finer mesh than the second lattice structure. The second lattice structure can, for example, form a carrier structure for the net-like structure of the first lattice structure. In this way, the division of functions between the two lattice structures or layers of the circumferential wall is ensured. The second lattice structure supports or fixes the first lattice structure in the blood vessel. By contrast, the first lattice structure can have such a fine mesh as to efficiently influence the flow of the blood into the aneurysm. Moreover, the first lattice structure can be flexible in such a way that the first lattice structure is easily able to follow a change of cross section of the blood vessel.

The wires of the first lattice structure preferably have a smaller cross-sectional diameter than the wires of the second lattice structure. The expansibility of the first lattice structure compared to the second lattice structure is thereby increased. Moreover, the first lattice structure can have a greater number of wires than the second lattice structure. This ensures that the first lattice structure has a finer mesh than the second lattice structure. In connection with a smaller cross-sectional diameter of the wires of the first lattice structure, the expansibility of the first lattice structure is further increased by comparison with the second lattice structure. The function of influencing the flow of blood into the aneurysm is improved.

Preferably, the first lattice structure forms an outer layer and the second lattice structure forms an inner layer of the tubular body. The second lattice structure can form a carrier structure, and the first lattice structure can form a net-like covering structure. The carrier structure supports the covering structure from the inside. This avoids a situation where the first lattice structure or the covering structure does not completely deploy upon expansion. The inner carrier structure, or the second lattice structure forming the inner layer, supports the first lattice structure across the entire length thereof.

In another preferred embodiment of the medical device, the first lattice structure has an axial lengthwise extent that is smaller than an axial lengthwise extent of the second lattice structure, in such a way that the first lattice structure covers the second lattice structure in some sections, in particular by at most 98%, at most 97%, at most 96%, at most 95%, at most 94%, at most 93%, at most 92%, at most 91%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5%, relative to the longer lattice structure. The aforementioned geometric ratios relate to the production state of the medical device. The production state corresponds substantially to an unloaded state. This means that the medical device is not exposed to an external force causing a compression of the tubular body. In other words, the tubular body is fully expanded in the production state.

It is also possible to adapt the device such that the aforementioned geometric ratios are present in the compressed state, wherein the first lattice structure is shorter than the second lattice structure. The aforementioned values are also disclosed in connection with the compressed state.

The difference in length between the two lattice structures can be increased, decreased or maintained constant upon expansion through adaptation of the foreshortening by means of a suitable choice of the braiding angles. For example, the difference in length can be shortened by at least 10%, in particular at least 20%, in particular at least 30%, in particular at least 40%, in particular at least 50%, in particular at least 60%, in particular at least 70%, in particular at least 80%, in particular at least 90% or by 100% length equalization). On the other hand, the difference in length can be increased by at least 2%, in particular at least 5%, in particular at least 10%, in particular at least 20%, in particular at least 30%, in particular at least 40%, in particular at least 50%, in particular at least 60%. At length equality, i.e. when the starting difference is 0 mm, the aforementioned values relate to the total length of one of the two lattice structures.

In absolute values, the difference in length can be changed (decreased or increased) as follows: 1 mm, 5 mm, 10 mm, 15 mm, and 20 mm. In the case of the decrease of the difference in length, these values are lower limits (at least) and in the case of the increase they are upper limits (at most).

Preferably, the second lattice structure is covered at least in some sections by the first lattice structure. The tubular body therefore has at least one section that has a multi-layer design.

The tubular body can have at least a third lattice structure. The third lattice structure preferably forms, together with the first lattice structure, the outer layer of the tubular body or of the circumferential wall of the tubular body. Generally, the individual separate layers of the circumferential wall can have several lattice structures. The lattice structures of individual layers can be movable relative to each other. It is important that independent layers each comprise at least one lattice structure that is movable in some sections relative to a lattice structure of an adjacent layer. It is preferable if the outer layer has several lattice structures. In the compressed and/or expanded state of the tubular body, the lattice structures of the outer layer, i.e. the first and third lattice structures, can be arranged flush with each other. The cross-sectional diameter of the tubular body in the compressed state is thus reduced. Alternatively, the lattice structures of the outer layer, i.e. the first and third lattice structures, can be arranged overlapping in the compressed and/or expanded state of the tubular body. This allows the second lattice structure to be covered over a relatively large surface area in an expanded state of the tubular body.

Preferably, the first lattice structure is connected at a proximal end, and the third lattice structure at a distal end, to the second lattice structure which forms the inner layer of the tubular body. In other words, the first and third lattice structures each have an end fixed to the second lattice structure and also a free end, wherein the free ends of the first and third lattice structures are arranged facing each other or adjacent to each other. In the compressed state of the tubular body, the free ends of the first and third lattice structures can be arranged flush with each other or in alignment. The free ends of the first and third lattice structures can also overlap each other in the compressed state of the tubular body.

Provision is preferably made that the first lattice structure and the third lattice structure overlap at least in some sections in a radially compressed state or a radially expanded state. On account of the foreshortening effect, which acts not only on the first and third lattice structures, but in particular on the second lattice structure that forms the inner layer of the tubular body, a shortening of the inner layer or second lattice structure takes place during the expansion of the tubular body. The two lattice structures that form the outer layer, i.e. the first and third lattice structures, moves closer to each other during the expansion of the tubular body. By suitable design of the individual lattice structures, it is possible to ensure that the first and third lattice structures overlap in some sections in the expanded state of the tubular body. During the expansion, the free ends of the first and second lattice structures thus move closer to each other and push over each other. This is the case when the effect of the foreshortening of the outer lattice structure is less than the effect of the foreshortening of the inner lattice structure. Preferably, the overlapping area of the first and third lattice structures is arranged at the treatment site in the area of the aneurysm. This has the effect that the outer layer of the tubular body has an increased expansibility in the area of the aneurysm, since the free ends of the first and third lattice structures are movable relative to each other. Under the influence of the blood flow, the free ends of the first and third lattice structures or of the overlap areas are therefore able to bulge into the aneurysm, such that a flow cushion is formed between the outer layer and the inner layer or the second lattice structure in the area of the aneurysm, in which cushion the flow energy of the blood flowing into the aneurysm is reduced and, consequently, the load applied to the aneurysm wall is minimized. It is also possible that the first and third lattice structures overlap each other in some sections both in the radially compressed state and also in the radially expanded state. The lattice structures, or the inner layer and the outer layer, can be designed in such a way that the first and third lattice structures do not overlap in the radially expanded state of the tubular body. In other words, the free ends of the first and third lattice structures in the radially expanded state can be arranged flush on each other or spaced apart from each other. The first and third lattice structures can thus be arranged in alignment with each other in the radially expanded state of the tubular body.

In another preferred embodiment, provision is made that the first lattice structure and the third lattice structure each comprise a proximal end, which is connected to the second lattice structure. In this case, the proximal end of the first lattice structure can be arranged at a distance from the proximal end of the second lattice structure. The outer layer can generally comprise several lattice structures which each form an axial section of the outer layer. The lattice structures, in particular the first and third lattice structures, each have a proximal end which is connected at points to the second lattice structure, i.e. the inner layer. The distal end of the first and third lattice structures is arranged free. The first and third lattice structures can overlap each other. In this way, the first and third lattice structures can form a scale-like outer layer. In particular, the first and third lattice structures can have a valve function, wherein the first and third lattice structures are advantageously positioned in the area of an aneurysm. The free ends of the first and/or third lattice structures can be deflected radially outward with respect to the inner layer of the tubular body, such that a catheter, for example a catheter for the positioning of coils, can be inserted into the aneurysm, wherein the catheter is guided through the meshes of the second lattice structure and deflects at least one free end of the first or third lattice structure radially outward, in order to gain access to the aneurysm.

In another preferred embodiment of the medical device, provision is made that the first lattice structure comprises a middle section and two edge sections delimiting the middle section. In the middle section, the first lattice structure has a smaller braiding angle than in the edge sections. Generally, provision can be made that the braiding angle of the respective lattice structure is variable. In other words, the braiding angle can change along the lattice structure, particularly in the longitudinal direction of the lattice structure. Preferably, the braiding angle changes along the first lattice structure in such a way that a smaller braiding angle is present in the middle section than in the edge sections. This ensures that the first lattice structure in the middle section has a greater radial expansibility compared to the edge sections. The middle section of the first lattice structure can therefore be expanded in the radial direction further than the edge sections. The expansibility is a result of the local flexibility in the middle section. However, the term flexibility is used primarily for the bending behavior of the whole device or of the whole stent.

An elongation of the vessel section in which the medical device is inserted is compensated by the edge sections during the systole. It is thus ensured that the axial ends of the first lattice structure, in particular a free end of the first lattice structure, do not significantly change their position. The positioning of the first lattice structure is instead maintained. By contrast, the middle section with the smaller braiding angle can utilize the smaller foreshortening effect during the systole. Specifically, the middle section of the first lattice structure can shorten during an elongation and simultaneous widening of the vessel section. Preferably, the middle section is positioned at the level of the aneurysm or of the aneurysm neck. This ensures that the middle section of the first lattice structure can bulge into the aneurysm or into the area of the aneurysm neck during the systole. As a result of the small braiding angle, the change in length is not significant. Thus, the middle section of the first lattice structure contributes to transferring the systolic pressure from the blood vessel into the aneurysm at least to a certain degree, such that the cells of the aneurysm wall are still under a mechanical load. Degeneration of the cells in the aneurysm wall is thus avoided.

In a preferred embodiment, the distance between the outer layer and the inner layer varies in the expanded state of the body, wherein the distance alternately decreases and increases at least in some sections. Specifically, the outer layer, in the expanded state of the body, has an undulating contour at least in some sections. The undulating contour is particularly effective in slowing down the flow.

The outer layer can have alternately disposed peaks and valleys, wherein at least some, in particular all, of the valleys are connected to the inner layer and/or are preshaped, in particular preshaped by heat treatment, and/or have another braiding angle than the peaks. In the connection, particularly the mechanical connection, of the valleys to the inner layer, it can be advantageous to connect a single valley or more than 1 valley, in particular more than 2 valleys, more than 3 valleys, more than 4 valleys, in particular all the valleys, to the inner layer and fix them. The fixed valleys are arranged proximally, i.e. on the same side as the proximal end of the outer layer. The distal end of the outer layer, and any unfixed valleys on the distal side, are movable in the axial direction. In a particularly preferred embodiment, only the proximal end is fixed which can be seen as a half valley proximally from the first peak. All complete valleys including the distal end are free and movable.

The undulating shape can be preshaped by mechanical forming or can be embossed and forms the rest state. In the catheter line, the undulating shape is stretched out and, upon release, it returns to the undulating rest state or starting state. When using a shape-memory material, the undulating shape can be embossed by a suitable heat treatment, utilizing the shape-memory effect. By means of different braiding angles, the radial stability can be locally influenced, such that some areas widen easily (peaks) and some areas widen less easily (valleys). The aforementioned options for utilizing the undulating contour can be used singly or in combination.

According to a subsidiary aspect, the invention is based on the concept of making available a system for medical uses and with a delivery system which comprises a flexible delivery element, in particular a guide wire. The delivery element is connected or connectable to the device. The system is preferably adapted in such a way that the device can be drawn back into the delivery system.

The illustrative embodiments and advantages that have been described in connection with the medical device apply equally to the system having such a device.

BRIEF DESCRIPTION OF THE DRAWINGS

The invention is explained in more detail below on the basis of illustrative embodiments and with reference to the attached schematic drawings, in which:

FIG. 6a shows a cross section through an aneurysm stent according to the prior art in a delivery system, wherein the aneurysm stent has a plurality of interwoven wall layers;

FIG. 6b shows a cross section through a medical device according to the invention, in a preferred illustrative embodiment, in a delivery system, wherein the device has two separate layers of lattice structures;

FIG. 7 shows a longitudinal section through a blood vessel with an aneurysm, wherein a medical device according to the invention, in a preferred illustrative embodiment, is inserted which comprises a first lattice structure with variable braiding angles;

DETAILED DESCRIPTION

Figure 1A:
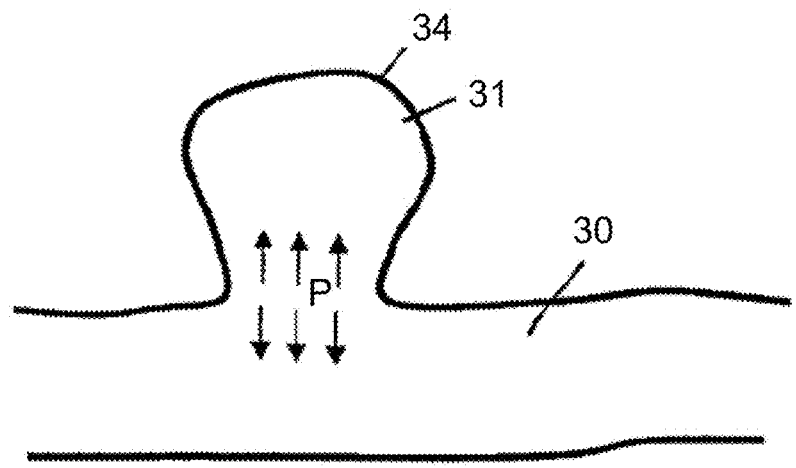
FIG. 1a shows a cross section through a blood vessel with an aneurysm and indicates the transfer of pressure into the aneurysm.

In FIG. 1a, the influence of the blood pressure on an aneurysm 31 in a blood vessel 30 is illustrated. The arrows show the transfer of the pressure P from the blood vessel 30 into the aneurysm 31. In general, the blood vessel 30 is subject to pressure fluctuations that are generated by the pulsatile blood flow or the pulsating activity of the heart. The pressure peaks occur during the so-called systole, i.e. the ejection phase of the heart activity. The pressure is at a minimum in the diastole, when the heart chambers fill with blood.

Figure 1B:
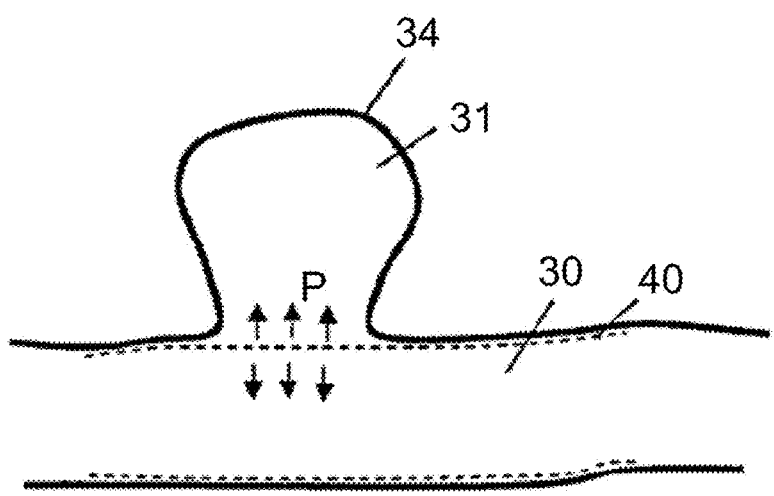
FIG. 1b shows the blood vessel according to FIG. 1a, with a conventional aneurysm stent inserted.
Figure 1C:
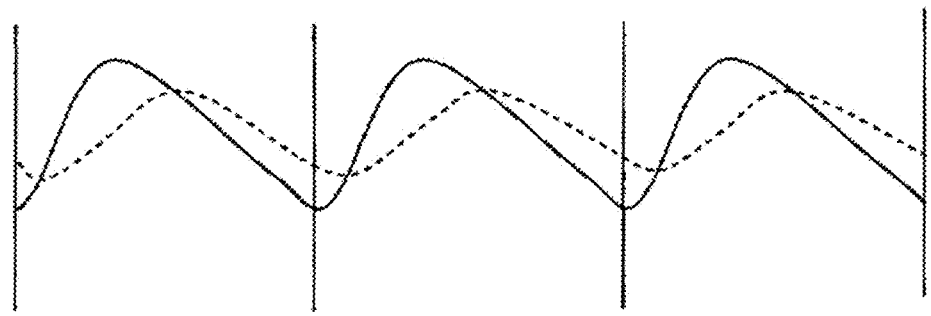
FIG. 1c shows a graph illustrating the pressure profile in the blood vessel and in the aneurysm when a conventional aneurysm stent is inserted.

In the prior art, the influence of the pressure fluctuations on the aneurysm 31 is affected by the use of a conventional fine-meshed aneurysm stent 40. For this purpose, the conventional aneurysm stent 40 is implanted in the area of the aneurysm 31 in the blood vessel 30 (FIG. 1b). The flow of blood between the blood vessel 30 and the aneurysm 31 is influenced by the structure of the conventional aneurysm stent 40, such that the pressure P transferred into the aneurysm 31 is on the one hand reduced and on the other hand acts on the aneurysm 31 with a time lag. FIG. 1c provides an illustration of the pressure profile in the blood vessel 30 (solid line) and in the aneurysm 31 (broken line) as covered by a conventional aneurysm stent 40. It can be seen clearly from the illustrated pressure profiles that the pressure in the aneurysm 31 rises and falls more slowly than in the blood vessel 30. The pressure curve in the aneurysm 31 is therefore flatter as a whole. The effect is all the more distinct the finer the mesh of the braid. The attenuation of the pressure is desirable but should not be too pronounced.

However, there is the possibility of the pressure reduction promoting a degeneration of the cells of the aneurysm wall 34. Particularly as a result of the reduced mechanical stress of the aneurysm wall 34, there is the danger of the cells of the aneurysm wall 34 degenerating or breaking down, thereby increasing the danger of a rupture even after insertion of an aneurysm stent 40.

Figure 2A:
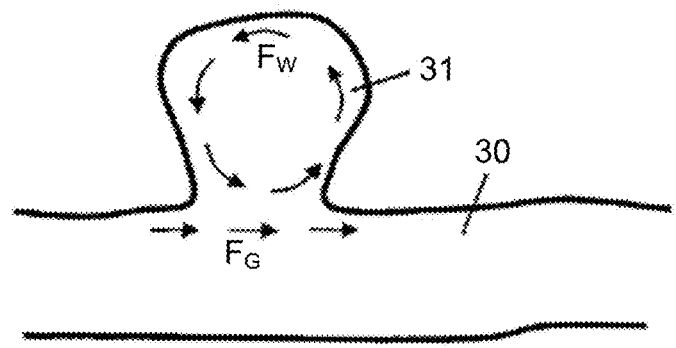
FIG. 2a shows a cross section through a blood vessel with an aneurysm and indicates the influence of the shear stress on the aneurysm.
Figure 2B:
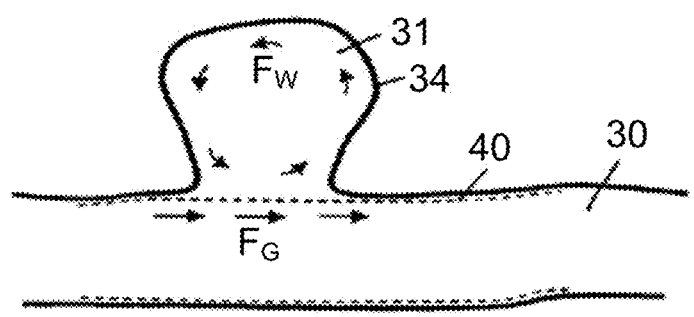
FIG. 2b shows the blood vessel according to FIG. 2a, with a conventional aneurysm stent inserted.

An aneurysm 31 is also influenced by the tangential blood flow or vessel flow $F_G$, as is illustrated in FIG. 2a. The vessel flow $F_G$ results in shear stresses occurring at the interfaces between the blood inside the aneurysm 31 and the blood inside the blood vessel 30, which leads to an eddy flow $F_W$ inside the aneurysm 31. The influence of the shear stress triggered by the vessel flow $F_G$ is reduced by the use of a conventional aneurysm stent 40, as is shown in FIG. 2b. The eddy flow $F_W$ inside the aneurysm 31 is thereby reduced. The reduction in the eddy flow $F_W$ has on the one hand the advantage that clotting in the aneurysm is improved. On the other hand, however, an excessive reduction of the eddy flow $F_W$ can promote the degeneration of cells of the aneurysm wall 34. Moreover, an exchange of blood between the blood in the aneurysm 31 and the blood vessel 30 is impeded, with the result that the aneurysm wall 34 is in some cases insufficiently supplied with nutrients. Too great a reduction of the flow can lead to the formation of clots that grow too rapidly.

Figure 3A:
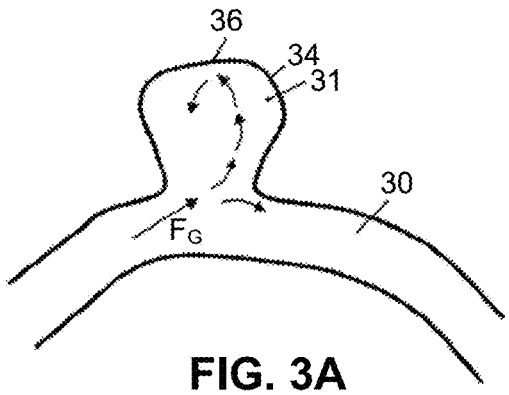
FIG. 3a shows a cross section through a blood vessel with an aneurysm and indicates the influence of a direct flow of blood into the aneurysm.
Figure 3B:
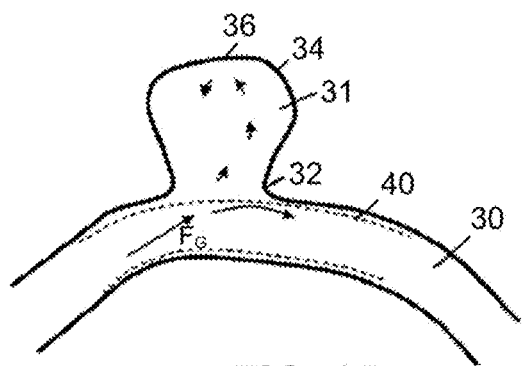
FIG. 3b shows the blood vessel according to FIG. 3a, with insertion of a conventional aneurysm stent having a small mesh size.
Figure 3C:
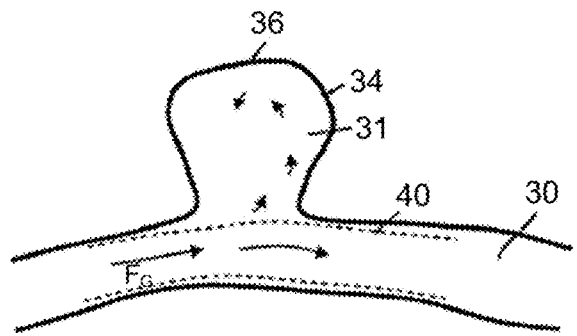
FIG. 3c shows the blood vessel according to FIG. 3a, with insertion of a conventional aneurysm stent having a large mesh size.

FIG. 3a shows the influence of the vessel flow $F_G$ on an aneurysm 31 in the untreated state, when the aneurysm 31 is arranged in a curvature of the blood vessel 30. The aneurysm 31 is in this case affected directly by the vessel flow $F_G$, since the vessel flow $F_G$ impinges locally on the aneurysm wall 34 in an attack region 36. The vessel flow $F_G$ is deflected in the attack region 36. The aneurysm wall 34 is exposed to an increased pressure load in the attack region 36. A conventional aneurysm stent 40 inserted into the blood vessel 30 offers a resistance to the vessel flow $F_G$, such that the flow fraction or blood fraction that flows into the aneurysm 31 is reduced. Thus, a conventional aneurysm stent 40 causes a reduction of the flow velocity into the aneurysm. Specifically, a through-flow $F_D$ through the aneurysm neck 32 of the aneurysm is reduced. At the same time, the resistance that the conventional aneurysm stent 40 offers to the blood flow or vessel flow $F_G$ brings about a change of the pressure wave or of the pressure profile within the aneurysm, thereby promoting the degeneration of the cells of the aneurysm wall 34. This applies in particular to stents with a fine-meshed structure, which additionally have a high degree of bendability and therefore fit well into the curvature of the blood vessel 30 (FIG. 3b). By contrast, conventional aneurysm stents 40 with a wide-meshed structure have a higher radial force, which has the effect that the blood vessel 30 stretches, as is shown in FIG. 3c. The elongation of the blood vessel 30 has the effect of reducing the fraction of the vessel flow $F_G$ conveyed directly into the aneurysm 31. However, the wide-meshed structure of known stents 40 of this type permits at the same time a large flow of blood into the aneurysm 31, particularly as a consequence of shear stresses, such that the aneurysm wall is under a considerable load.

Figure 4A:
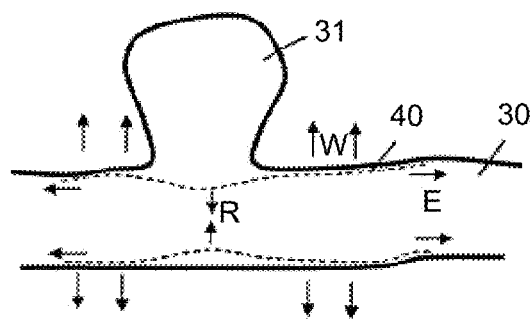
FIG. 4a shows a longitudinal section through a blood vessel, with an aneurysm and with an inserted conventional aneurysm stent, and indicates the influence that pulse-induced changes in the blood vessel have on the aneurysm stent.
Figure 4B:
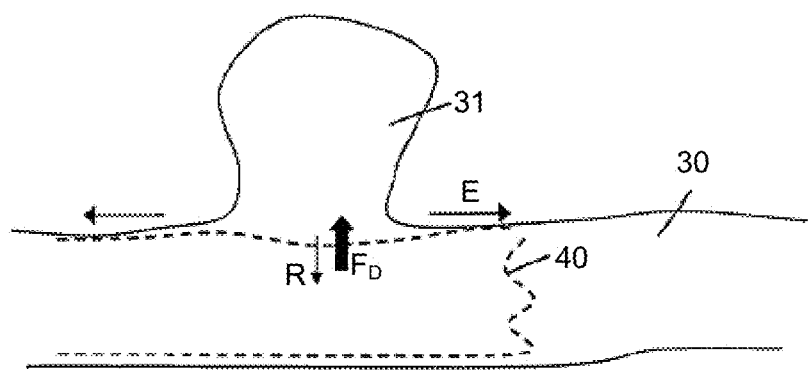
FIG. 4b shows the blood vessel according to FIG. 4a and indicates an increased flow of blood into the aneurysm through the meshes of a conventional aneurysm stent, under the influence of a systolic blood pressure.

Conventional aneurysm stents 40, in particular conventional aneurysm stents 40 with a fine-meshed structure, are additionally influenced by the periodic vascular changes of the blood vessel 30. FIG. 4a shows that during the systole, i.e. during a pressure peak in the profile of the blood pressure, the blood vessel 30 on the one hand experiences radial expansion, i.e. has a widening W, and on the other hand is stretched in the longitudinal direction. In addition to the widening W, an elongation E of the blood vessel 30 also takes place during the systole. On account of the foreshortening effect explained at the outset, the widening W and elongation E of the blood vessel 30 cause a narrowing R of the conventional aneurysm stent 40. The narrowing R is seen in particular in the area of the aneurysm 31. As a result, the circumferential wall of the conventional aneurysm stent 40 moves away from the aneurysm neck 32, as is shown in FIG. 4a. The considerable danger of dislocation of the conventional aneurysm stent 40 is heightened by the widening of the vessels and the narrowing R. Moreover, the influence on the eddy flow $F_W$ is reduced in the area of the aneurysm 31. The effectiveness of the treatment of the aneurysm 31 is therefore diminished. Specifically, the structure of conventional aneurysm stents 40 shows substantially an inverse reaction during the systole. Whereas the blood pressure assumes a maximum locally in the systole, at the same time the aneurysm stent 40 narrows. In other words, the circumferential wall of the conventional aneurysm stent 40 moves against the rise in pressure. In this way, the through-flow FD through the meshes of the conventional aneurysm stent 40 into the aneurysm 31 is increased. This effect is illustrated in FIG. 4b.

Figure 5A:
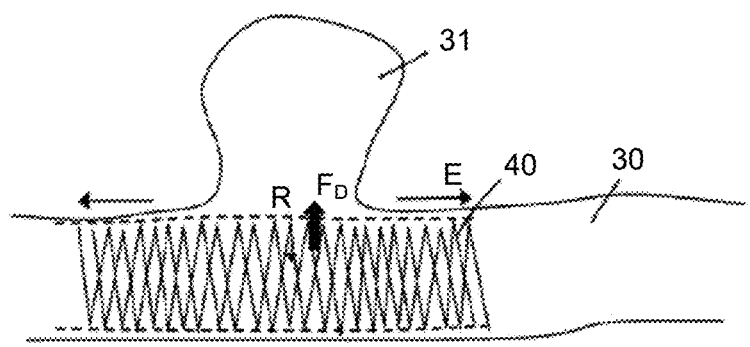
FIG. 5a shows a longitudinal section through a blood vessel with an aneurysm, and with insertion of a conventional aneurysm stent having a large braiding angle.

Conventional aneurysm stents 40 with a large braiding angle, as shown in FIG. 5a, are known from the prior art. Conventional aneurysm stents 40 with a large braiding angle have the property of being able to follow an elongation E of the blood vessel, without experiencing severe narrowing R. As a whole, the structure of aneurysm stents 40 of this kind is relatively dimensionally stable in the radial direction (low compliance), such that they additionally have a strong influence on the transfer of pressure from the blood vessel 30 into the aneurysm 31. The pressure P in the aneurysm 31 is reduced as a whole, as is shown in FIG. 1c.

Figure 5B:
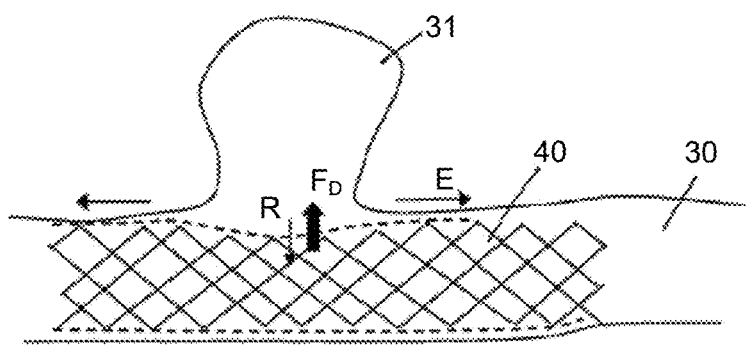
FIG. 5b shows the blood vessel according to FIG. 5a, with insertion of a conventional aneurysm stent having a small braiding angle.

FIG. 5b shows a conventional aneurysm stent 40 that has a small braiding angle. Known stents of this kind have increased flexibility, but this means that a narrowing R of the conventional aneurysm stent 40 occurs in the event of an elongation E of the blood vessel 30, with the disadvantages described above.

FIG. 6a shows a cross-sectional view of the known aneurysm stent 40 according to DE 601 28 588 T2 in the compressed state inside a delivery system 20. The known aneurysm stent 40 has two layers of wire braids, wherein the wire braids of the two layers are interwoven. A first wire braid has first wires 41, which have a larger cross-sectional diameter than second wires 42 of a second layer of the conventional aneurysm stent 40. The interweaving of the first and second wires 41, 42 means that, in the compressed state inside the delivery system 20, the first and second wires 41, 42 are in a complex arrangement and need a large amount of space in the compressed state.

By contrast, in the illustrative embodiment according to the invention, provision is made that the medical device comprises a tubular body 10. The device is designed in particular as a stent. The tubular body 10 has a circumferential wall, which comprises a first lattice structure 11 and a second lattice structure 12. The first and second lattice structures 11, 12 each form separate layers 14, 15 of the circumferential wall. The lattice structures 11, 12 of the tubular body 10 according to the invention are therefore independent of each other at least in some sections, preferably along the whole of the lattice structure. The lattice structures 11, 12 are connected to each other at points. In particular, the circumferential wall of the tubular body can comprise a circumferential line in which the first lattice structure 11 is connected to the second lattice structure 12. In particular, a single connecting line between the first lattice structure 11 and the second lattice structure 12 can be provided which extends in the circumferential direction about the tubular body 10. It is explicitly noted that the connection between the first lattice structure 11 and the second lattice structure 12, and possibly further lattice structures, does not take place across an extensive surface area but instead substantially in a line shape.

As a result of the separate layers that each comprise a lattice structure 11, 12, the space taken up by the tubular body 10 in the compressed state is reduced, as is shown in FIG. 6b. FIG. 6b shows a cross section through the tubular body 10 which, in the expanded state, comprises two layers 14, 15 that are arranged in the shape of a hollow cylinder (see FIG. 12 for example) and that each have a lattice structure 11, 12. An inner layer 15 is provided, which has the second lattice structure 12. An outer layer 14, which surrounds the inner layer 15, comprises the first lattice structure 11. The layered and concentric arrangement of the two lattice structures 11, 12 is maintained in the compressed state, as is illustrated in FIG. 6b.

The wires 112 of the first, outer lattice structure 11 have a cross-sectional diameter that is smaller than the cross-sectional diameter of the wires 122 of the second, inner lattice structure 12. The tubular body according to FIG. 6b is arranged inside a delivery system 20. As a result of the reduced space taken up by the tubular body 10 compared to conventional aneurysm stents 40, it is possible to use a smaller delivery system 20. The medical device can therefore be introduced into smaller blood vessels.

It will also be seen from FIG. 6b that the first lattice structure 11 and the second lattice structure 12 are arranged coaxially one inside the other. The first lattice structure 11 and the second lattice structure 12 are also movable relative to each other at least in some sections. Specifically, the first and second lattice structures 11, 12 are movable relative to each other outside the linear or punctiform connection between the first and second lattice structures 11, 12. The relative mobility applies in particular to the individual wires 112, 122 of the first and second lattice structures 11, 12. In particular, the wires 112 of the first lattice structure 11 can slide on the wires 122 of the second lattice structure 12, and vice versa.

In the illustrative embodiment according to the invention shown in FIG. 6b, the wires 112 of the first lattice structure 11 are thicker than the wires 122 of the second lattice structure 12. It is also possible that the wires 112, 122 of the lattice structures 11, 12 have the same cross-sectional diameter. Moreover, the wires 122 of the second lattice structure 12 can have a larger cross-sectional diameter than the wires 112 of the first lattice structure 11. For the improved crimpability of the tubular body 10, or of the device generally, it is advantageous if the inner layer 15 is composed of a relatively smaller number of thicker wires 122 and the outer layer 14 is formed by a comparatively greater number of thinner wires.

In general, it has proven advantageous if one layer 14, 15 has a finer mesh structure than the other layer 15, 14. In other words, one of the two layers 14, 15 can comprise more wires 112, 122 than another layer 14, 15. The wires 112, 122 can in this case be thinner than the wires 112, 122 of the other layer 15, 14. It is possible that the more finely meshed layer 14, 15 has a larger or a smaller braiding angle than the comparatively wide-meshed layer 15, 14. Combinations of the aforementioned variants are possible.

It is particularly preferable if the fine-meshed layer is the outer layer 14 and the wide-meshed layer is the inner layer 15.

Generally, the device preferably has a tubular body 10 comprising an outer layer 14 and an inner layer 15. The device can be a stent. The outer layer 14 is formed by the first lattice structure 11 and the inner layer 15 is formed by the second lattice structure 12. The second lattice structure 12 preferably has a wide-meshed wire braid. By contrast, the first lattice structure 11 has a fine-meshed wire braid. The wide-meshed wire braid of the second lattice structure 12 thus forms a carrier 18, whereas the fine-meshed wire braid of the first lattice structure 11 forms a net 19.

Generally, it is possible that both layers, that is to say the outer layer 14 and the inner layer 15, are designed alike. The layers 14, 15 can thus have the same fine-meshed structure and/or the same number of wires and/or the same wire thickness and/or the same braiding angles. All combinations of the aforementioned variants are possible. The connection of the lattice structures means that they are oriented relative to each other or have braiding patterns oriented relative to each other.

It will further be noted that the invention is not limited to structures having two layers. Instead, the scope of the application also claims and discloses tubular bodies 10 or stents that comprise a circumferential wall with three or more separate layers. Some or all of the layers can be constructed according to the invention.

Particularly advantageous configurations of the carrier 18 are described below:

The carrier 18 or the second lattice structure 12 preferably has at most 32 wires 122, in particular at most 24, in particular at most 20, in particular at most 16, in particular at most 12, in particular at most 8, in particular at most 6. The wires 122 of the second lattice structure 12 or of the carrier 18 preferably have a cross-sectional diameter of at least 40 µm, in particular at least 50 µm, in particular at least 60 µm, in particular at least 68 µm, in particular at least 75 µm, in particular at least 84 µm, in particular at least 100 µm. This applies to medical devices for use in blood vessels 30 that have a cross-sectional diameter of 2 mm to 6 mm. If the blood vessel 30 to be treated has a cross-sectional diameter of greater than 6 mm, the wires 122 of the second lattice structure 12 or of the carrier 18 preferably have a cross-sectional diameter of at least 40 µm, in particular at least 50 µm, in particular at least 60 µm, in particular at least 68 µm, in particular at least 75 µm, in particular at least 84 µm, in particular at least 100 µm, in particular at least 150 µm, in particular at least 200 µm.

In principle, the circumferential wall of the tubular body 10 can comprise more than one carrier 18.

Generally, the carrier 18 or the second lattice structure 12 has a high degree of bendability, and the bending of the second lattice structure 12 or of the carrier 18 along a longitudinal axis of the second lattice structure 12 requires a relatively high bending force or a relatively high bending moment. This means that the carrier 18 causes an elongation of a curved blood vessel 30. The carrier 18 thus contributes to reducing the flow component of vessel flow $F_G$ flowing directly into the aneurysm 31. The direct inflow of the vessel flow $F_G$ into the aneurysm 31 is thus reduced.

The carrier 18 can in the widest sense be a supporting structure or carrying structure for the net 19. It is preferable that the carrier 18 is arranged coaxially inside the net 19. In this way, the carrier 18 or the second lattice structure 12 can be used to stabilize the net 19 or the first lattice structure 11. In particular, the expansion behavior of the net 19 can be controlled by the carrier 18.

The carrier 18 preferably forms the inner layer 15 of the tubular body 10. Alternatively, the carrier 18 can form the outer layer 14. In this way, the carrier 18 permits good stabilization of the blood vessel 30 and an expansion of the tubular body 10 up to a pre-defined cross-sectional diameter. Overall, the carrier 18 permits good and controllable expansion of the tubular body 10 and of the net inside the carrier 18.

Preferred variants of the net 19 or of the first lattice structure 11 are described below:

The net 19 preferably has finer meshes than the carrier 18. Thus, the net 19 mainly has the function of influencing the flow in relation to the aneurysm 31. The fine-meshed structure of the net 19 is preferably limited to the extent that flow of blood into the aneurysm 31 is not completely prevented. Instead, the net 19 is intended, on the one hand, to prevent a rupture of the aneurysm 31 and, on the other hand, to maintain sufficient nutrient supply and mechanical loading of the aneurysm wall 34, such that a degeneration of the cells of the aneurysm wall 34 is avoided. As regards the fine-meshed nature of the net 19, it is therefore advantageous if the net 19 has at most 48 wires 112, in particular at most 44, in particular at most 40, in particular at most 36, in particular at most 32, in particular at most 24, in particular at most 20, in particular at most 16, in particular at most 12. The net 19 is stabilized by the carrier 18, such that the net 19 does not have to meet any particular requirements as regards the radial force. In order to improve the crimpability, provision is therefore advantageously made to reduce the wire diameter of the wires 112 of the first lattice structure 11 or of the net 19 in relation to the cross-sectional diameter of the wires 122 of the second lattice structure 12 or of the carrier 18. Preferably, the wires 112 of the first lattice structure 11 or of the net 19 have a cross-sectional diameter of at most 77 µm, in particular at most 51 µm, in particular at most 46 µm, in particular at most 41 µm, in particular at most 36 µm, in particular at most 26 µm, in particular at most 20 µm. This applies to the use of the tubular body 10, or generally of the medical device, in blood vessels 30 that have a vessel diameter of 2 mm to 6 mm. If the vessel has a diameter of greater than 6 mm, it is advantageous if the wires 112 of the first lattice structure 11 or of the net 19 have a cross-sectional diameter of at most 155 µm, in particular at most 105 µm, in particular at most 77 µm, in particular at most 51 µm, in particular at most 46 µm, in particular at most 41 µm, in particular at most 36 µm, in particular at most 26 µm, in particular at most 20 µm.

The net 19 preferably forms the outer layer 14 of the tubular body 10. The highly flexible net 19 is supported by the carrier 18 during the expansion of the tubular body 10 and forced into the expanded state. The interaction between carrier 18 and net 19 prevents a situation where the net 19 does not deploy sufficiently in the blood vessel 30. The carrier 18 forming the inner layer 15 preferably supports the net 19 along the entire length of the net 19.

The first lattice structure 11 and the second lattice structure 12 are connected to each other at points. The connection of the first lattice structure 11 to the second lattice structure 12 preferably takes place at a proximal end of the tubular body 10. In particular, the first lattice structure 11 has a proximal end 110, which is connected to a proximal end 120 of the second lattice structure 12.

It will be noted here that, in the context of the application, proximal elements are arranged closer to the user than distal elements.

Figure 8:
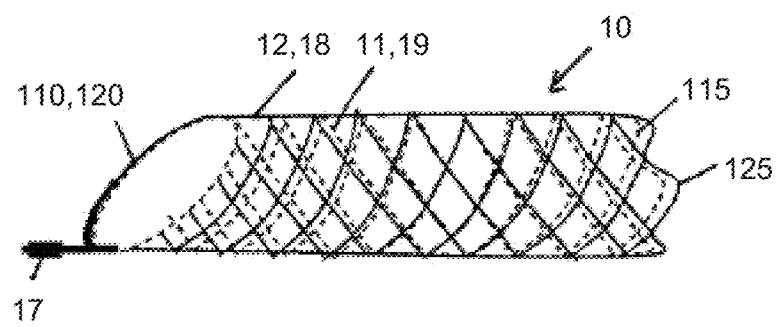
FIG. 8 shows a perspective side view of a medical device in another illustrative embodiment according to the invention.

The first lattice structure 11 and the second lattice structure 12 preferably each have an obliquely tapering proximal end 110, 120. The wires 112, 122 of the first lattice structure 11 and of the second lattice structure 12 converge at the obliquely arranged proximal ends 110, 120. The converging wires 112, 122 are connected to each other. Such a connection of the first and second lattice structures 11, 12 is shown by way of example in FIG. 8. According to the illustrative embodiment in FIG. 8, the connection of the converging wires 112, 122 of the first lattice structure 11 and of the second lattice structure 12 is effected by a connecting sleeve 17. The converging wires 112, 122 of the first and second lattice structures 11, 12 can run parallel to each other in the area of the connecting sleeve 17 or can be twisted together. Moreover, provision can be made that the wires 112 of the first lattice structure 11 completely enclose the wires 122 of the second lattice structure 12 in the area of the connecting sleeve 17. This corresponds substantially to the arrangement as shown in the cross-sectional view according to FIG. 6b. Conversely, it is also possible that the wires 122 of the second lattice structure 12 completely enclose the wires 112 of the first lattice structure 11 in the area of the connecting sleeve 17. Other types of connection are possible. For example, the first lattice structure 11 and the second lattice structure 12, or the net 19 and the carrier 18, can be connected to each other in a middle area of the tubular body 10. Moreover, a connection between the first and second lattice structures 11, 12, between net 19 and carrier 18, at a distal end of the tubular body 10 is conceivable, e.g. at the loops of the lattice structure. A connection in the oblique area is possible.

Preferably, the lattice structures 11, 12 have a wire braid that has an oblique profile at a proximal end 110, 120 or generally at an axial end of the respective lattice structure 11, 12. Such wire braids are described in the later published German patent application No. 10 2009 056 450, which was filed by the applicant and which by reference is incorporated in full into the present application.

In order to achieve the dual function according to the invention, namely that of sufficiently fixing the tubular body 10 or stent in the blood vessel 30, and that of deliberately influencing the flow into an aneurysm 31 without promoting a degeneration of the muscle cells of the aneurysm wall 34, it is expedient to deliberately adjust the braiding angles of the individual wire braids or lattice structures 11, 12. Preferred illustrative embodiments for different braiding angles are described below:

In conventional aneurysm stents 40, provision is made to choose the braiding angle to be as large as possible, so that the aneurysm neck 32 is closed as far as possible. The disadvantage of such treatment possibilities lies in an increased risk of bleeding, as a result of degeneration of the cells of the aneurysm wall and the formation of increasingly large fresh clots, a high degree of foreshortening, which makes positioning of the conventional aneurysm stents 40 difficult, and an insufficient adaptation to variable vessel diameters. It generally applies that, upon a change of diameter, the change of length of a conventional aneurysm stent is all the greater, the larger the chosen braiding angle. This makes a reproducible and adjustable configuration of known aneurysm stents 40 difficult.

Therefore, in the medical device, provision is advantageously made for the braiding angle to be limited. In particular, it has proven expedient if the braiding angle is at most 70°, in particular at most 67°, in particular at most 65°, in particular at most 63°, in particular at most 60°. The braiding angle relates to the acute angle that is formed between a wire of the lattice structure and the longitudinal axis of the tubular body 10. It was found that with a braiding angle of 60°, a shortening of the respective lattice structure 11, 12 during expansion, i.e. during the transfer of the tubular body 10 from a compressed state to an expanded state, amounts to 50%. This means that the lattice structure 11, 12 with a braiding angle of 60°, which has a length of 40 mm in the compressed state, i.e. inside the delivery system 20, has a length of 20 mm or slightly over 20 mm in the expanded state, particularly in the blood vessel 30.

Preferably, a braiding angle for the first lattice structure 11 or the second lattice structure 12 is provided which is at most 60°, in particular at most 59°, in particular at most 58°, in particular at most 57°, in particular at most 56°, in particular at most 55°, in particular at most 54°, in particular at most 53°, in particular at most 52°, in particular at most 51°, in particular at most 50°, in particular at most 45°. This has the effect that the shortening of the tubular body 10, during the expansion or the release into a blood vessel 30, varies within an acceptable range. The foreshortening effect is thereby reduced. Since the tubular body 10 is usually overdimensioned, that is to say has a larger cross-sectional diameter in the production state than in the implanted state within the blood vessel 30, the respective lattice structure 11, 12 in the blood vessel 30 has a braiding angle of approximately 30° to 50°, such that the tubular body 10 has comparatively good flexibility.

In this connection, it will be noted that the dimensions specified for the medical device, in particular for the tubular body 10, in the context of the application relate in principle to the production state, unless indicated otherwise.

The first lattice structure 11 and the second lattice structure 12, or the net 19 and the carrier 18, can have different braiding angles. This means that different foreshortening effects arise during the expansion of the tubular body 10. In other words, upon release of the tubular body 10 from a delivery system 20, the carrier 18 and the net 19, which have different braiding angles, exhibit a different foreshortening behavior. This also applies in the implanted state when blood pressure fluctuations resulting from the pulsatile blood flow act on the tubular body 10. The two layers 14, 15, i.e. the carrier 18 and the net 19, are therefore influenced differently by the pulsatile blood flow. In a particularly preferred manner, provision can be made that a gap 16 forms between the carrier 18 and the net 19, or between the outer layer 14 and the inner layer 15, in particular between the first lattice structure 11 and the second lattice structure 12. The gap 16 can act as a cushion. The gap can be obtained, for example, when the braids are connected in a punctiform manner in one area and have different braiding angles in at least one area. The braiding angle can vary along the longitudinal axis.

In a preferred variant, the braiding angle of the carrier 18 is smaller than the braiding angle of the net 19. This means that, upon release from a delivery system, the net 19 shortens to a greater extent than the carrier 18. In this way, the positioning of the tubular body 10 as a whole can be simplified, since the carrier 18 exhibits a minor foreshortening effect during the expansion. Generally, the tubular body 10 is released from a delivery system 20, when the delivery system with the compressed tubular body 10 has been guided to the treatment site. The delivery system 20 is then pulled in the proximal direction, whereas the tubular body 10 is kept fixed in position. In order to compensate for the foreshortening, provision can be made for a proximal end of the tubular body 10 to be pushed slightly in the distal direction simultaneously with the proximal movement of the delivery system 20. This ensures that the outer layer 14 of the tubular body 10 is not pulled along the vessel wall 35 of the blood vessel 30 and does not damage the vessel wall 35. The fact that the carrier 18 has a smaller braiding angle than the net 19 means that, during the expansion of the tubular body 10, the proximal end 120 of the second lattice structure 12 or of the carrier 18 has to be pushed only a short distance in the distal direction against the foreshortening. This therefore facilitates the positioning of the tubular body 10 or of the multi-layer stent. By contrast, the net 19 or the first lattice structure 11 experiences greater shortening, as a result of which the fine mesh of the net 19 increases during the expansion. In this way, a very considerably fine mesh can be achieved using an overall smaller number of wires 112, 122.

Moreover, the outer element, or the outer lattice structure, can have a smaller foreshortening than the inner element, or the inner lattice structure, such that the outer element bears well on the vessel wall.

Figure 9:
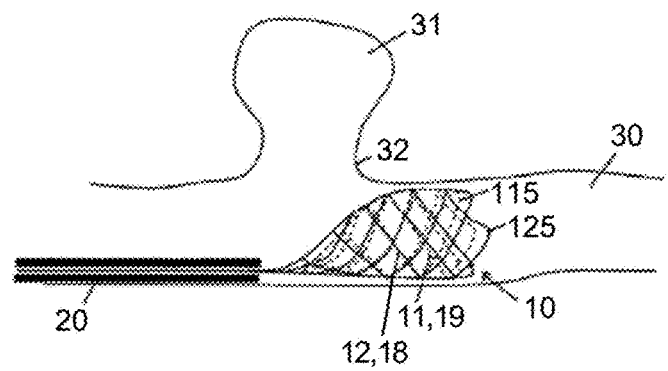
FIG. 9 shows the medical device according to FIG. 8 during release from a delivery system.

FIG. 9 shows the release of the tubular body 10 from a delivery system 20 into a blood vessel 30. Upon release of a distal end of the tubular body 10, the distal end 115 of the first lattice structure 11 and the distal end 125 of the second lattice structure 12 first of all deploy simultaneously and at the same height. When the delivery system 20 is pulled farther back in the proximal direction, a relative movement takes place between the first lattice structure 11 and the second lattice structure 12, since, with further release of the tubular body 10, the foreshortening effect of the first lattice structure 11 is more pronounced than in the second lattice structure 12. A proximal displacement of the net 19 with respect to the carrier 18 thus takes place. This proximal displacement of the net 19 with respect to the carrier 18 is caused by the larger braiding angle of the net 19. Preferably, the net 19 is arranged on the outside of the carrier 18. The net 19 thus forms the outer layer 14 of the circumferential wall of the tubular body 10. By contrast, the carrier 18 forms the inner layer 15 of the circumferential wall. Alternatively, provision can be made that the net 19 forms the inner layer 15 and the carrier 18 forms the outer layer 14. This has the advantage that the net 19 can slide on wires 122 of the carrier 8 during the expansion. The net 19 arranged on the outside has a smaller braiding angle than the carrier 18, and therefore also a smaller foreshortening effect then the carrier 18.

When the net in the preferred embodiment forms the outer layer 14, the contact between the tubular body 10 and the vessel wall 35 of the blood vessel 30 is established initially by the net 19. To compensate for the slight foreshortening of the carrier 18, the lattice structures 11, 12, or the proximal end of the tubular body 10, are pushed in the distal direction. The inner carrier 18, or the inner layer 15, thus moves in the distal direction. The carrier 18 can slide along the vessel wall 35. Since the carrier 18 has a relatively small braiding angle, it is possible to push the carrier 18 along the vessel wall 35, without the carrier 18 or the second lattice structure 12 being squashed together. With the comparatively small braiding angle of the carrier 18, the wires 22 of the second lattice structure 12, or of the carrier 18, have a directional component which is particularly pronounced in the longitudinal direction, that is to say parallel to the longitudinal axis, of the tubular body 10. Thus, pushing the carrier 18 or the second lattice structure 12 does not necessarily lead to a change in the pitch or braiding angle of the wires 122 of the second lattice structure 12. Thus, by means of the small braiding angle of the carrier 18, squashing together of the carrier 18 is avoided during a distal movement of the carrier 18.

Figure 10:
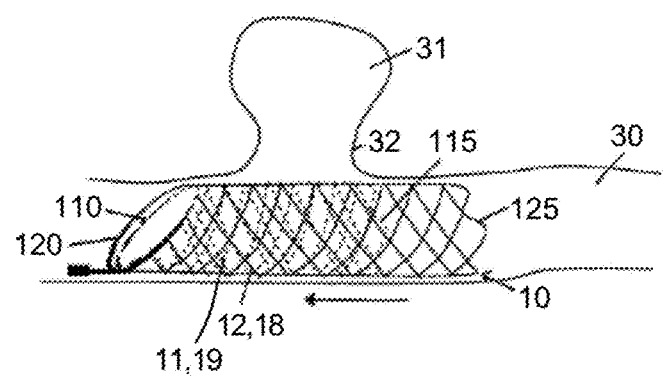
FIG. 10 shows the medical device according to FIG. 8 in an arrangement inside a blood vessel.

After complete expansion of the tubular body 10, the carrier 18 or the second lattice structure 12 has a greater lengthwise extent than the net 19 or the first lattice structure 11. The net 19 is therefore subject to a greater foreshortening effect than the carrier 18, such that the carrier 18, in the expanded state of the tubular body 10, is not covered completely by the net 19 but only partially or in some sections (FIG. 10). In the compressed state, the net 19 is longer than the carrier 18. In the expanded state, the length of the net 19 and of the carrier 18 can correspond to each other or the difference in length can diminish.

Figure 11:
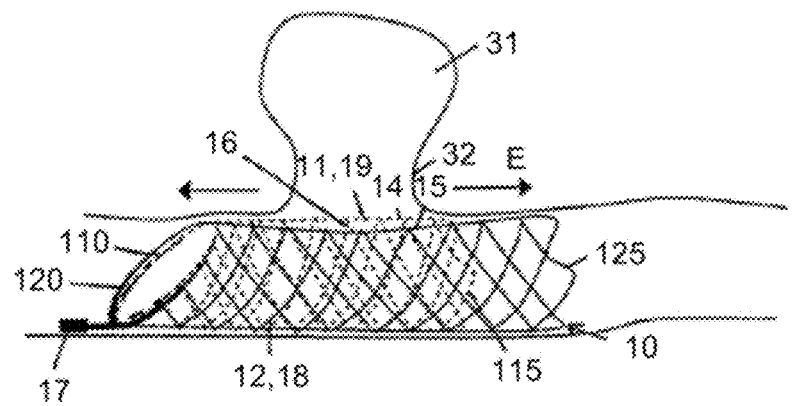
FIG. 11 shows the medical device according to FIG. 10 under the influence of an elongation of the blood vessel.

As a result of the different braiding angles between the first lattice structure 11 and the second lattice structure 12, the first lattice structure 11 and the second lattice structure 12, or the net 19 and the carrier 18, have a different behavior during pulsation of the vessel. In the implanted state inside the blood vessel 30, a gap 16 can form between the first lattice structure 11 and the second lattice structure 12 or between the net 19 and the carrier 18, in particular during the systole. As a result of the elongation E of the blood vessel 30 during the systole, the foreshortening effect means that the carrier 18, which has a comparatively small braiding angle, is narrowed at least in some sections, or has a narrowing R at least in some sections. By contrast, during the systole and the elongation E of the blood vessel, the net 19 exhibits no narrowing R, or at least much less narrowing R. Thus, a gap 16 or an interstice or cushion forms between the carrier 18 and the net 19. FIG. 11 shows as an example the behavior of the lattice structures 11, 12, or of the carrier 18 and net 19, with different braiding angles during an elongation E of the blood vessel.

Figure 12:
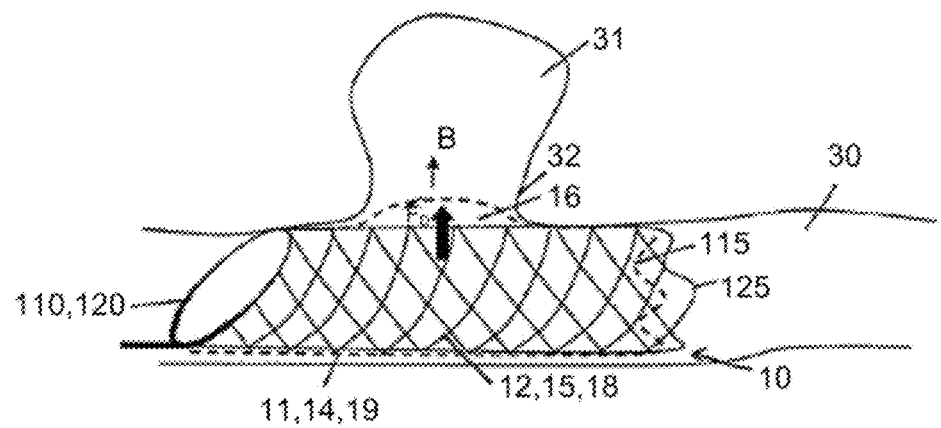
FIG. 12 shows the medical device according to FIG. 10 under the influence of a systolic blood pressure.

The net 19 is preferably adapted such that the net 19 can follow the pulsation of the blood vessel 30. In particular, the net 19 has an increased mobility with respect to the carrier 18, which can be achieved, for example, by suitably small wire diameters and/or suitable adjustment of the braiding angle. During the systole, i.e. the rise in blood pressure, a through-flow $F_D$ is brought about, with blood flowing out of the blood vessel 30 into an aneurysm 31 and leading to a volume increase in the aneurysm 31. The high degree of expansibility of the net 19 allows a portion of the net 19 to move radially outward or be deflected radially outward, with the net 19 following the movement of the blood in some sections. A flow of blood through the meshes of the net 19 is thus impeded. The expansibility of the net 19 is preferably adjusted such that the net 19, in terms of its deflection by the blood stream into the aneurysm 31, has an inertia or a resistance to the blood stream. The net 19 thus follows the rise in blood pressure during the systole by means of a radially outward movement. The flow of blood through the meshes of the net 19 into the aneurysm 31 is at the same time reduced. FIG. 12 shows the radial deflection of the net 19 in some sections, under the influence of the systolic rise in blood pressure. The transfer of pressure takes place only to a certain extent, thus resulting in clot formation and reduced degeneration of the cells. The transfer of pressure can be controlled by means of the possibility of being able to adjust the expansibility of the net 19, for example through the choice of the braiding angle.

The deflection of the net 19 into the aneurysm 31 has several advantages. On the one hand, the flexible net 19 permits the transfer of the pressure wave into the aneurysm. Although a stream of blood into the aneurysm is impeded, the pressure P is, by contrast, transferred into the blood volume of the aneurysm 31. A periodic loading of the cells of the aneurysm wall 34 is thus maintained, thereby counteracting a degeneration of the cells. At the same time, the direct through-flow of blood, i.e. the through-flow $F_D$, is reduced, thereby promoting the endothelialization of the tubular body 10. The colonization of endothelial cells and the adherence of the endothelial cells to the tubular body 10 is made easier by the reduced through-flow $F_D$. In particular, the closure of the meshes of the lattice structures 11, 12 is made easier, since there is only a slight through-flow $F_D$, if any, through the meshes of the first lattice structure 11 or of the net 19.

It has generally been shown that it is advantageous to make available a lattice structure which is flexible in such a way that it can be deflected at least in some sections into the aneurysm 31. This is made possible, for example, by a lattice structure which has a comparatively small braiding angle. However, a lattice structure of this kind experiences increased narrowing R if the blood vessel 30, for example on account of the pulsation, is subject to an elongation E. Lattice structures with a large braiding angle do not exhibit this effect. Specifically, a lattice structure with a large braiding angle permits considerable elongation, without any significant change of the cross-sectional diameter. However, lattice structures of this kind do not permit outward bulging in some sections, for example into an aneurysm 31.

Both effects are achieved with the device according to the invention, the functions being assigned to different lattice structures 11, 12. The second lattice structure 12 or the carrier 18 permits the precise and reliable positioning of the tubular body 10 in the blood vessel 30. By contrast, the net 19 makes it possible to influence the flow of blood into the aneurysm 31, while at the same time permitting a transfer of the blood pressure. The post-operative risk of a rupture of the aneurysm 31 is thus reduced.

FIG. 7 shows a further illustrative embodiment of the medical device, wherein the net 19 or the first lattice structure 11 has different braiding angles. In particular, the first lattice structure 11 comprises a middle section 111 and two edge sections 116, wherein the middle section 111 is arranged between the edge sections 116. In the middle section 111, the first lattice structure 11 has a smaller braiding angle than in the edge sections 116. The comparatively larger braiding angle in the edge sections 116 has the effect that the edge sections 116 compensate for the elongation E of the blood vessel 30, because they are able to undergo elongation without a significant change of diameter. In particular, transition sections 113 form between the middle section 111 and the edge sections 116, which transition sections 113 are highlighted by the dotted lines in FIG. 7. In the transition sections 113, a shortening K takes place in an orientation counter to the elongation E of the blood vessel 30. The middle section 111 has a greater expansibility than the edge sections 116, such that the middle section 111, under the influence of a systolic rise in blood pressure, can have a greater shortening than the edge sections 116. The middle section 111 can thus follow the rise in blood pressure, such that the net 19 or the first lattice structure 11 in the middle section 111 can bulge out into the aneurysm 31 or can form a bulge B. For the sake of clarity, the carrier 18 or the second lattice structure 12 is not shown in FIG. 7.

Figure 13:
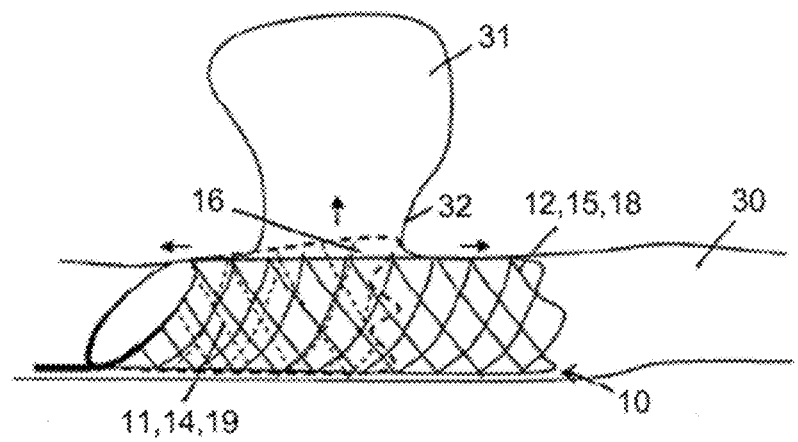
FIG. 13 shows a perspective side view of a medical device in another illustrative embodiment according to the invention, under the influence of an elongation of the blood vessel, wherein an outer layer of the circumferential wall comprises a shorter lattice structure than an inner layer.

A further illustrative embodiment is shown in FIG. 13, wherein provision is made that the net 19 has a shorter lengthwise extent than the carrier 18. Particularly in the implanted state inside the blood vessel 30, the net 19 or the first lattice structure 11 has a substantially shorter lengthwise extent than the carrier 18 or the second lattice structure 12.

Preferably, the tubular body 10 is positioned in the blood vessel 30 in such a way that the distal end 115 of the first lattice structure 11 or of the net 19 is arranged in the area of the aneurysm neck 32. The distal end 115 of the first lattice structure forms a free end. By contrast, the proximal end 110 of the first lattice structure 11 is connected to the proximal end 120 of the second lattice structure 12. The free end or distal end 115 of the first lattice structure 11 can expand radially outward. The distal end 115 of the first lattice structure 11 or of the net 19 is thus deflected radially outward into the aneurysm 31 or into the area of the aneurysm neck 32. In other words, the net 19 can be deflected in some sections into the aneurysm 31. During a systolic rise in blood pressure, the net 19 therefore moves with the blood pressure increase into the aneurysm 31, such that the through-flow $F_D$ through the meshes of the net 19 is reduced. The distal end is longer and ensures the adherence.

Figure 14:
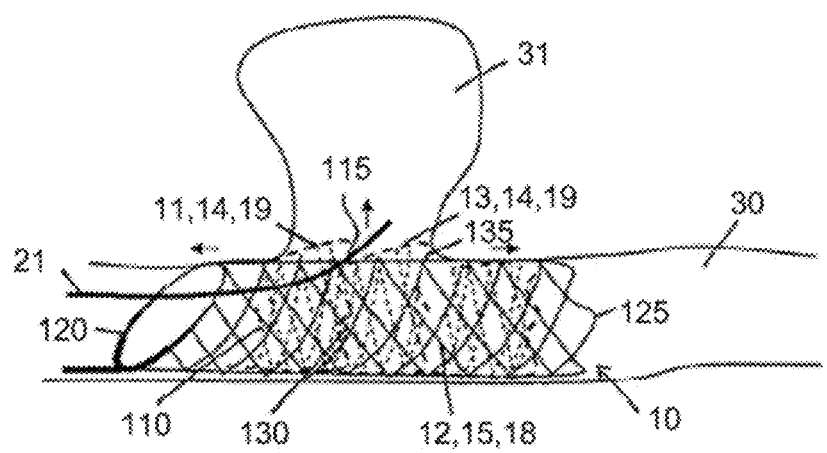
FIG. 14 shows a perspective side view of a medical device in another illustrative embodiment according to the invention, under the influence of an elongation of the blood vessel, wherein the outer layer of the circumferential wall comprises two lattice structures arranged in succession.

A further illustrative embodiment is shown in FIG. 14, wherein the tubular body 10 comprises a circumferential wall which has an inner layer 15 and an outer layer 14. The inner layer 15 is formed by the second lattice structure 12, which is designed as carrier 18. The outer layer 14 has the first lattice structure 11 and a third lattice structure 13, wherein the first lattice structure 11 and the third lattice structure 13 each form a net 19. The first and third lattice structures 11, 13 are each connected with their proximal ends 110, 130 to the second lattice structure 12. The distal ends 115, 135 of the first lattice structure 11 and of the third lattice structure 13 are arranged free. The proximal end 130 of the third lattice structure 13 is connected to the second lattice structure 12 substantially at the level of the distal end 115 of the first lattice structure 11. This results substantially in a scale-like arrangement of the first and third lattice structures 11, 13. The first lattice structure 11 and the third lattice structure 13 can also overlap each other at least in some sections or can be arranged at a distance from each other.

The first lattice structure 11 and the third lattice structure 13, or the nets 19, can have a valve-like function. By means of the free mobility of the distal ends 115, 135, the nets 19 or the first and third lattice structures 11, 13 permit a certain transfer of pressure into the aneurysm 31. At the same time, the valve function of the nets 19 permits the delivery of additional treatment devices into the aneurysm 31. Such treatment devices can comprise a coil catheter 21, for example.

In principle, the invention is not limited to two nets 19 or two lattice structures 11, 13 that form the outer layer 14. Instead, provision is also made, within the context of the invention, that three or more nets 19 or lattice structures 11, 13 form the outer layer 14 of the circumferential wall of the tubular body 10.

Figure 15A:
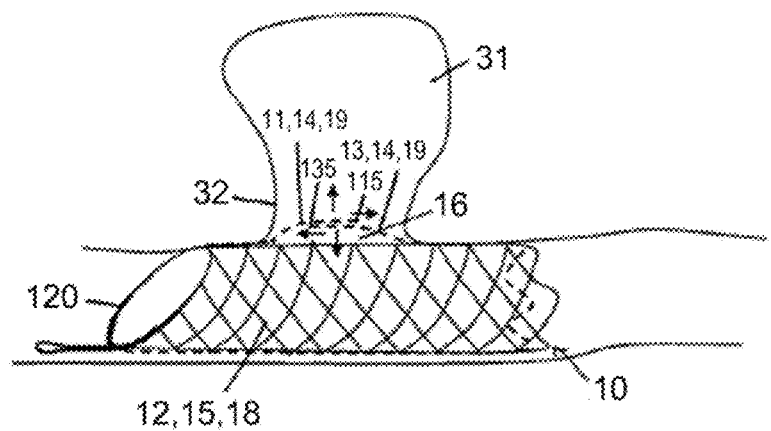
FIG. 15a shows a perspective side view of a medical device in another illustrative embodiment according to the invention in the implanted state, wherein the outer layer of the circumferential wall comprises two lattice structures overlapping each other in the expanded state of the device.

FIG. 15a shows a further illustrative embodiment, which differs from the illustrative embodiment according to FIG. 14 in that the first lattice structure 11 and the third lattice structure 13 are oriented substantially in opposite directions. Specifically, in the illustrative embodiment according to FIG. 15a, provision is made that the first lattice structure 11 comprises a proximal end 110 which is connected to the proximal end 120 of the second lattice structure 12. The distal end 115 of the first lattice structure 11 is arranged free. By contrast, the third lattice structure 13 comprises a distal end 135 which is connected to the distal end 125 of the second lattice structure 12. The proximal end 130 of the third lattice structure 13 is arranged free. Moreover, in the illustrative embodiment according to FIG. 15a, provision is made that the free ends, i.e. the distal end 115 of the first lattice structure 11 and the proximal end 130 of the third lattice structure 13, overlap each other. This applies at least to the expanded or implanted state of the tubular body 10. Alternatively, provision can also be made that the first and third lattice structures 11, 13 do not overlap each other in the expanded or implanted state of the tubular body 10 and instead are arranged in alignment with each other, as is shown in FIG. 16a.

Moreover, in the illustrative embodiment according to FIG. 15a, provision is advantageously made that the nets 19, or the first and third lattice structures 11, 13, overlap each other in the expanded state, but are arranged in alignment with each other in the compressed state of the tubular body 10. For this purpose, provision is advantageously made that, during the expansion of the tubular body 10, the carrier 18 or the second lattice structure 12 is shortened to a greater extent than the nets 19. At least one net 19 or a plurality of nets 19 have in particular a smaller braiding angle than the carrier 18, such that the carrier 18 is considerably shortened during the expansion of the tubular body 10, as a result of which the nets 19 overlap in the expanded state. The overlapping ensures that the aneurysm neck 32 is completely covered. At the same time, the mobility of the free ends of the first and third lattice structures 11, 13 permits a relative movement of the two lattice structures 11, 13 or nets 19 to each other, such that an efficient transfer of pressure into the aneurysm 31 is enabled. At the same time, the overlapping of the first and third lattice structures 11, 13 in some sections increases the fineness of the mesh in the area of the aneurysm neck 32 and has an advantageous influence on the flow of blood into the aneurysm 31. By contrast, to achieve this kind of mesh fineness with a single net 19 or a single lattice structure 11, a comparatively larger delivery system 20 is needed.

Figure 15B:
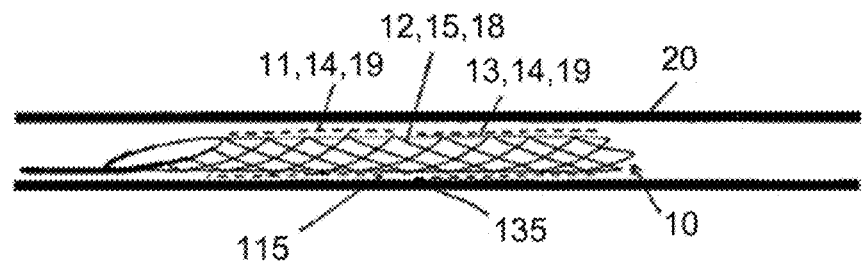
FIG. 15b shows the device according to FIG. 15a in a compressed state inside a delivery system.

The aligned arrangement of the nets 19 inside the delivery system 20, i.e. in the compressed state, reduces the crimp diameter, such that small delivery systems 20 can be used (FIG. 15b).

Figure 16A:
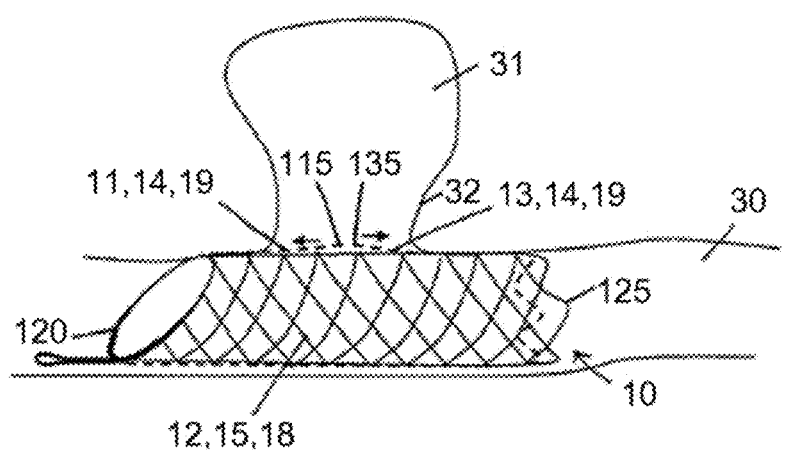
FIG. 16a shows a perspective side view of a medical device in another illustrative embodiment according to the invention, wherein the outer layer of the circumferential wall comprises two lattice structures arranged in alignment in the expanded state of the device.

In the illustrative embodiment according to FIG. 16a, provision is made that, in contrast to the illustrative embodiment according to FIG. 15a, the mutually opposite nets 19 or the first and third lattice structures 11, 13 have a comparatively larger braiding angle. This increases the fine mesh of the individual nets 19 or of the first and third lattice structures 11, 13. A configuration of this kind has the effect that the nets 19 shorten to a great extent during the expansion. In order to permit an exact positioning of the tubular body 10 in the blood vessel, the carrier 18 or the second lattice structure 12 advantageously has, by contrast, a comparatively small braiding angle, such that the foreshortening effect is reduced.

Figure 16B:
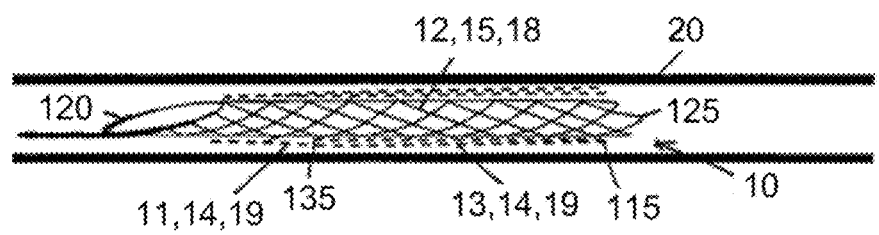
FIG. 16b shows the device according to FIG. 16a in a compressed state inside a delivery system.

In the expanded or implanted state of the tubular body 10, the first lattice structure 11 and the third lattice structure 13 or the two nets 19 are preferably arranged in alignment with each other. The free ends of the first and third lattice structures 11, 13 can touch each other, such that the aneurysm 31 or the aneurysm neck 32 is completely covered by the first and third lattice structures 11, 13. In the compressed state inside the delivery system 20, by contrast, the first and third lattice structures 11, 13 are superposed, as is shown in FIG. 16b. In order to achieve the smallest possible compressed cross-sectional diameter despite the superposing or overlapping of the first and third lattice structures 11, 13 in the delivery system 20, provision is made that the nets 19, or the first and third lattice structures 11, 13, have a small number of wires. As a result of the comparatively large braiding angle that the first and third lattice structures 11, 13 adopt in the blood vessel 30, a very fine-meshed structure is guaranteed even with a small number of wires. Moreover, the cross-sectional diameter in the compressed state of the tubular body 10 is reduced on account of the small number of wires. The nets can also be arranged on the inside.

Figure 17:
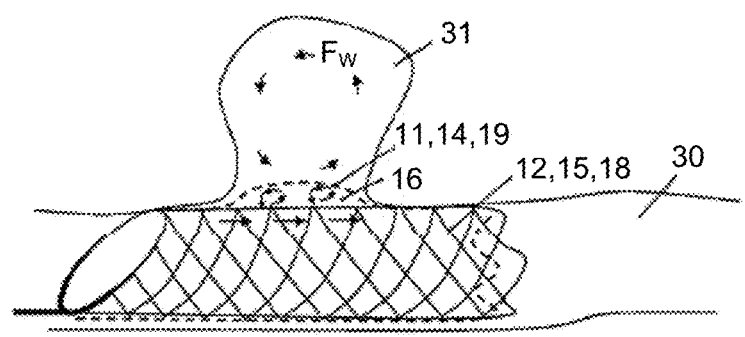
FIG. 17 shows the device according to FIG. 12, wherein the reduced eddying in the aneurysm is indicated by a cushion area between the first and second lattice structures of the tubular wall.

As has already been described, the adoption of different braiding angles in separate layers 14, 15 of the tubular body permits the formation of a gap 16 between the layers 14, 15. In particular, in the expanded state of the tubular body 10, the net 19 can lift away from the carrier 18. The formation of a gap in a suitably configured medical device is shown in FIG. 17. The gap 16 permits additional influence of the flow conditions in the aneurysm 31. By means of the gap 16, or the distance between the net 19 and the carrier 18, a cushion is basically obtained in which flow eddies arise that are produced by shear stresses between the blood inside the cushion or gap 16 and the vessel flow $F_G$. As a result of the flow eddies in the gap 16, an energy loss occurs, by which means the flow velocities inside the aneurysm 31 are reduced. In particular, the vessel flow $F_G$ does not cause a direct eddy flow $F_W$ in the aneurysm but initially an eddy flow in the gap 16. Although an exchange of blood is permitted between the blood vessel 30 and the aneurysm 31, the flow velocities are reduced. At the same time, the expansibility of the net 19 permits a transfer of pressure into the aneurysm 31, such that, in order to preserve the cells of the aneurysm wall 34, nutrients are conveyed to the cells via the blood and, moreover, a mechanical stress is maintained that counteracts degeneration. At the same time, the net may permit a reduced or moderate transfer of pressure.

Figure 18:
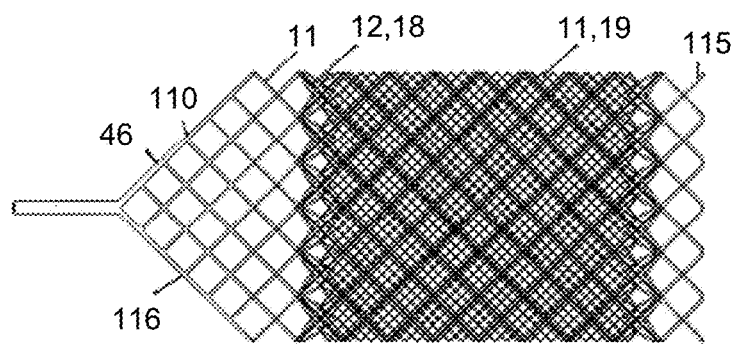
FIG. 18 shows the developed view of a device in an illustrative embodiment according to the invention in which two lattice structures are superposed.

An illustrative embodiment of an overall system or of a device with carrier 18 and net 19 is shown in FIG. 18. The device according to FIG. 18 forms a retractable braid on account of the oblique tip in the proximal area of the device. The device is a stent, in particular an aneurysm stent. The basic design of the device, particularly in the area of the oblique tip, is disclosed in DE 10 2009 056 450 filed by the applicant. The basic design entails a braid of wire elements with a series of end meshes or end loops which delimit an axial braid end, wherein the end meshes comprise outer wire elements which form a terminal edge 46 of the braid and merge into inner wire elements arranged inside the braid. A first section of the terminal edge 46 and a second section of the terminal edge 46 in each case have several outer wire elements which together form a peripheral border of the terminal edge 46. The border is adapted in such a way that the axial braid end of the hollow body can be drawn into a delivery system. The outer wire elements of the first section for forming the terminal edge 46 are arranged immediately downstream of the latter and each have a first axial component extending in the longitudinal direction of the hollow body. The outer wire elements of the second section for forming the terminal edge 46 are arranged in immediate succession along the latter and each have a second axial component which extends in the longitudinal direction of the hollow body and is counter to the first axial component. Both axial components are referred to the same peripheral direction of the border.

This configuration of the proximal end of the device applies to all the illustrative embodiments of this application in which the device has an oblique tip pointing in the proximal direction.

In the illustrative embodiment according to FIG. 18, the first lattice structure 11 of the net 19 is arranged congruently over the second lattice structure 12 of the carrier 18. The second lattice structure 12 of the carrier 18 is therefore visible only in the area of the net 19 where the strands or individual wires of the two lattice structures 11, 12 are not congruent. The strands or wires of the second lattice structure 12 of the carrier 18 are indicated in black in the area of the net 19 and have a larger diameter than the wires of the net 19.

In the area of the proximal tip or at the proximal end 110 of the first lattice structure 11, and at the distal end 115 of the first lattice structure 11, the two lattice structures 11, 12 are congruent, such that only the first lattice structure 11 shown on top in FIG. 18 can be seen. The second lattice structure 12 is arranged underneath the first lattice structure 11 in the developed view. In the tubular (three-dimensional) body 10, the first lattice structure 11 with the net 19 is arranged radially to the outside and the second lattice structure 12 of the carrier 18 is arranged radially to the inside.

The transition from the net 19 to the strands in the area of the tip of the first lattice structure 11 is such that in each case four individual wires of the net 19 or four individual strands of the net 19 are brought together to form two strands, which are in turn brought together in the proximal direction to form one strand, from which the lattice structure of the tip is formed. Another number of wires or strands, each successively combined with one another or brought together, is possible. The strands guided in the proximal direction extend into the terminal edge 46 and are connected there as per DE 10 2009 056 450.

The area of the tip of the carrier 18 is configured accordingly, wherein the lattice structure 12 of the carrier 18 is formed from individual wires with a larger diameter than the individual wires of the first lattice structure 11. Alternatively, the second lattice structure 12 can also be formed from several strands that each consist of individual wires.

In the area of the tip, therefore, the strands or wires of the two lattice structures 11, 12 run in parallel and are congruent. The same applies to the distal end 115.

In the area of the net 19, the wires or strands likewise run in parallel, but they are not congruent. Instead, the wires of the net 19 overlap the lattice cells formed by the carrier 18.

Figure 19:
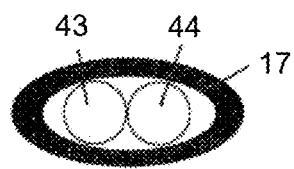
FIG. 19 shows a cross section through the device according to FIG. 18 in the area of the connecting sleeve.

In the illustrative embodiment according to FIG. 18, the punctiform connection between the first lattice structure 11 and the second lattice structure 12 takes place outside the two lattice structures 11, 12. Specifically, the two lattice structures 11, 12 are connected in the area of the two common end strands 43, 44 in which all the wires of the respective lattice structures 11, 12 are brought together. The two end strands 43, 44 are shown in cross section in FIG. 19. The connection is provided by the sleeve 17. Instead of the sleeve 17, the two end strands 43, 44 can be connected in some other way. For example, the thinner wires of the first lattice structure 11, which forms the outer layer in the illustrative embodiment according to FIG. 18, can be mounted onto the thicker wires of the carrier 18 and, for example, twisted. For example, the thicker wires of the carrier 18 are twisted together in an inner strand. The thinner wires of the net 19 or of the first lattice structure 11 are twisted radially to the outside on the inner strand. Other types of connection are possible. In addition or alternatively, the wires can be connected by a sleeve, for example by the sleeve 17 according to FIG. 19. The sleeve can be crimped onto the wires and/or welded to the wires. The wires can be twisted and connected as described above. Alternatively, the wires can also be arranged loosely alongside each other. The strands of both lattice structures 11, 12 can also be arranged alongside each other, wherein the sleeve 17 encloses and connects both strands, as is shown in FIG. 19. The sleeve 17 can be circular or oval in cross section, for example as is shown in FIG. 19. The oval contour promotes the apposition to the vessel wall.

The punctiform connection of the two lattice structures 11, 12 outside the surface of the lattice structures 11, 12 has the effect that the lattice structures 11, 12 are arranged loosely one above the other and are therefore movable relative to each other. At the same time, the two lattice structures 11, 12 are oriented such that the patterns of the lattice structures 11, 12 in combination with each other form a higher-order common pattern, as can be seen clearly in FIG. 18.

The connection between the two lattice structures 11, 12 or the two braids can also take place in the area of the loops. For example, the thin wires of the net 19 can be wound around the thicker wires of the carrier 18 or twisted together with them. This applies for each number of wires. For example, each loop of the net 19 consists of two wires which are wound about the single wire of the loop of the carrier 18. Another number of wires or wire combinations is possible. The connection of the wires by sleeves is also possible.

Further possibilities for the punctiform connection of the two lattice structures 11, 12 include the connection being made only in the area of the terminal edge 46, for example by twisting. Another punctiform connection can be obtained by means of the wires of the two lattice structures 11, 12 being twisted together, or otherwise connected, for example welded, in the whole oblique area or in the whole area of the tip. The area of the tip terminates where the two lattice structures 11, 12 merge into the area of the closed cylindrical jacket surface. The distal end can correspondingly have a punctiform connection between the two lattice structures 11, 12.

Figure 20:
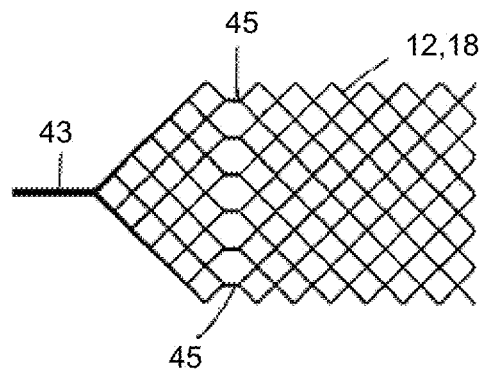
FIG. 20 shows a developed view of a carrier for a device in a further illustrative embodiment according to the invention.
Figure 21:
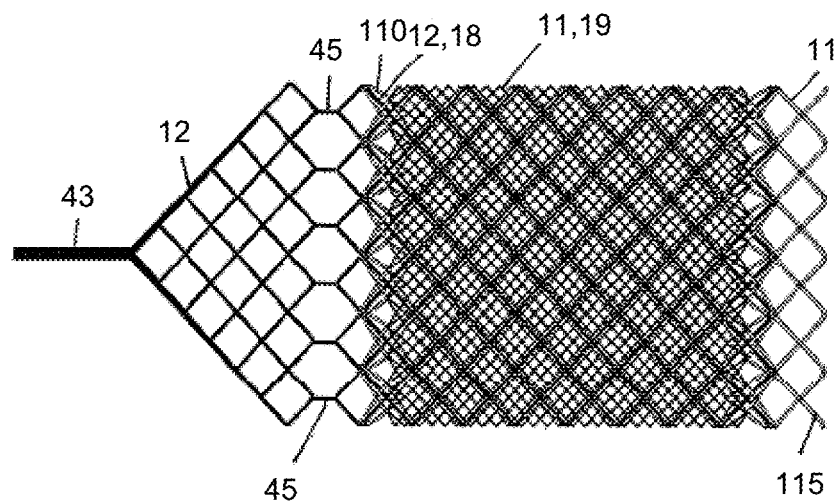
FIG. 21 shows the developed view of a device in an illustrative embodiment according to the invention, with the carrier according to FIG. 20.

A further illustrative embodiment of a device according to the invention is shown in FIG. 21, in which a carrier 18 according to FIG. 20 is used. The carrier 18 according to FIG. 20 is adapted to be connected in a middle area to a further braid, in particular to a further lattice structure. For this purpose, the second lattice structure 12 of the carrier 18 has anchoring sites 45 at which the first lattice structure 11 can be secured to the net 19. The basic design of the lattice structure 12 of the carrier 18 corresponds to the basic design according to FIG. 18 or DE 10 2009 056 450, at least as regards the area of the tip.

In the area of the anchoring sites 45, the wires of the carrier 18 are twisted and extend substantially parallel to the longitudinal axis of the device.

The combined structure is shown in FIG. 21, where the first lattice structure 11 with the net 19 is arranged radially to the outside, and the carrier 18 radially to the inside, in the tubular (three-dimensional) body 10. The first lattice structure 11 with the net 19 partially overlaps the second lattice structure 12, there being no overlap in the area of the tip or terminal edge 46. Therefore, in FIG. 21, the lattice structure 12 of the carrier 18 is visible in the area of the tip. As in the illustrative embodiment according to FIG. 18, the lattice structure 12 of the carrier 18 continues in the area of the net 19 and is clearly visible under the net 19 by means of the thicker wires or strands that are shown in black. At the distal end 115, the end loops of the first lattice structure 11 cover the distal end of the second lattice structure 12 of the carrier 18.

The punctiform connection of the two lattice structures 11, 12 is achieved by means of the wires of the net structure 19 converging in the area of the twisted elements of the carrier or of the anchoring sites 45. In the area of the anchoring sites 45, the wires of the two lattice structures 11, 12 run parallel to each other and are oriented parallel to the axis of the stent. In the area of the anchoring sites 45, the wires can be twisted or connected in some other way, for example by welding, adhesive bonding, soldering, or by a separate means such as a connecting sleeve, in particular a c-shaped connecting sleeve. The c-shaped connecting sleeve has the advantage that the two systems or lattice structures 11, 12 can initially be overlapped during production and then connected by the sleeve. Alternatively, the thinner wires of the net 19 can be wound around the thicker wires of the carrier 18 or twisted together with them, specifically in the area of the anchoring sites 45.

Alternatively, the connection can also be made at intersections of the carrier 18. A common aspect of these embodiments is that the connection of the two lattice structures 11, 12 is punctiform, i.e. not across the entire surface of the two lattice structures, and instead only within a limited area. The punctiform connection according to FIG. 21 is a linear connection in the circumferential direction and is composed of individual connection points or connection sites. The connection points are formed, for example, at the anchoring sites 45, where the two lattice structures are connected locally to each other to a limited degree.

The distal end of the net 19 can have open ends. The advantage of this is the ease of production. However, the distal end can also have closed loops. In addition to the proximal connection in the area of the anchoring sites 45, a punctiform connection can also be made at the distal end of the net.

The invention is suitable for endovascular interventions, particularly for the treatment of aneurysms in blood vessels. For this purpose, the medical device is preferably designed as a stent. The invention is not limited to a medical device or a stent that comprises braided lattice structures. Instead, the lattice structures can also be formed by cutting a corresponding structure from a solid material, particularly from a tubular solid material. The use of lattice braids or wire braids is advantageous in view of the preferred fine-meshed structure.

Figure 22:
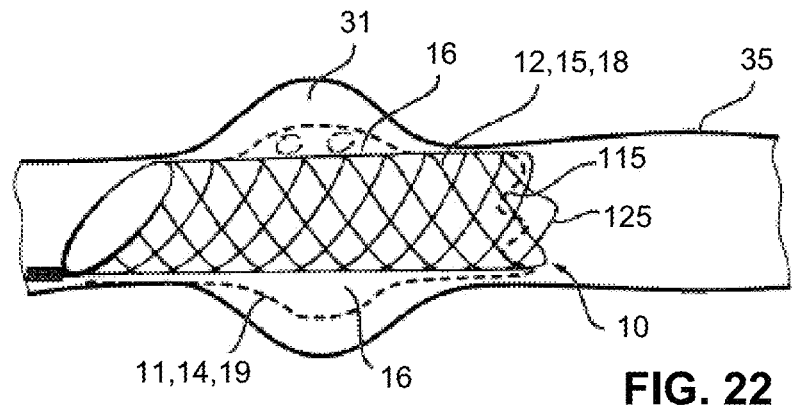
FIG. 22 shows a perspective side view of a medical device in an illustrative embodiment according to the invention that is used to treat a fusiform aneurysm.
Figure 23:
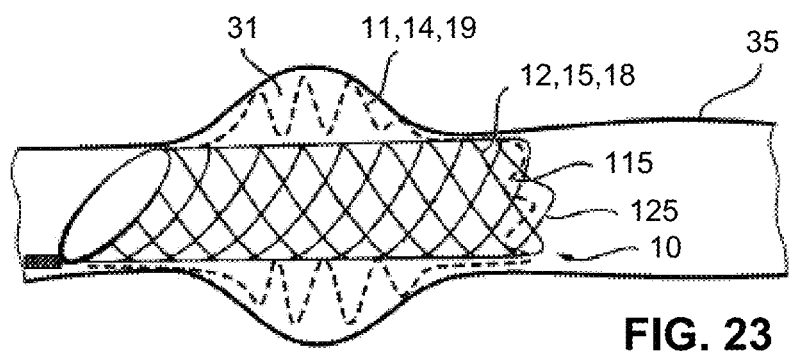
FIG. 23 shows a perspective side view of a medical device in a further illustrative embodiment according to the invention that is used to treat a fusiform aneurysm.

FIGS. 22 and 23 show that the multiple braid, with an outer braid or outer layer 14 relatively movable in the axial direction and radial direction, is suitable for the treatment of different types of aneurysms. As is shown, the multiple braid is suitable for the treatment of fusiform aneurysms, which develop in a spindle shape all the way around the vessel circumference. In a fusiform aneurysm, the inner layer 15 or the second lattice structure 12 forms, as has been described above, the carrier 18 which positions the system in the vessel. As is shown in FIG. 22, the inner layer 15 bears on the vessel wall 35 upstream and downstream of the aneurysm 31 that is to be treated. The outer layer 14 expands uniformly on the entire circumference of the tubular body 10 and lifts away from the latter, as is shown in FIG. 22. In this way, an annular gap 16 forms in the area of the fusiform aneurysm and ensures the eddying of the blood stream in this area. The locally limited securing of the outer layer 14 on the one hand and the low stiffness of the outer layer 14 on the other hand permit the spindle-shaped expansion of the outer layer 14, such that the outer layer 14 protrudes at least partially into the fusiform aneurysm. The possibilities of locally limited securing are described above and are disclosed in connection with this illustrative embodiment. The stiffness of the outer layer 14 is less than the stiffness of the inner layer 15. The outer layer 14 is more flexible than the inner layer 15.

In a lateral aneurysm (saccular aneurysm), the outer layer 14 moves laterally away from the inner layer 15, as is shown in FIG. 12 for example. The outer layer 14 is therefore pressed away from the side on which there is no aneurysm and bulges into the neck of the aneurysm.

The function of the multiple braid as described in connection with FIG. 22 is disclosed and claimed in connection with all of the illustrative embodiments.

The bulging or widening of the outer layer 14 or of the outer braid can be set automatically by suitable conditioning in the context of a heat treatment when the tubular body 10 is released from the catheter. This means that the outer braid or the outer layer 14 is widened in the rest state and thus lifts away from the inner layer 15. The widening of the outer braid can be stamped on a middle area of the outer braid or stamped exclusively on a middle area of the outer braid. As is shown in FIG. 22, the shape of the widening can be adapted for the treatment of a fusiform aneurysm and can extend in an annular shape around the tubular body 10 or have a spindle shape. Alternatively, the shape of the widening can be adapted to the treatment of a saccular aneurysm and form exclusively to the side or only on one side of the body 10. The outer layer 14 or the outer braid can, for example, be shaped and heat-treated on a suitably curved mandrel. The braid ends or the end areas of the braid of the outer layer 14 remain in contact with the braid of the inner layer 15. This means that the end areas of the outer layer 14 are located on the same plane or the same jacket surface as the braid of the inner layer 15. In the middle area, or generally between the end areas, the braid of the outer layer 14 lifts away from the inner layer 15.

Alternatively or in addition, the widening, as has been described above, can be obtained from the different braiding angle between the inner layer 15 and the outer layer 14 or between the respective braids.

The above-described constrained widening of the outer layer 14 by suitable heat treatment is disclosed and claimed as a possible option in connection with all of the illustrative embodiments. Moreover, it is disclosed and claimed in this connection that at least the outer layer 14 or the braid of the outer layer 14 is produced from a shape-memory material, for example from nitinol or another shape-memory material customarily used in medical engineering and permitting a heat-induced change of shape. Alternatively, the constrained change of shape can also be obtained by an elastic deformation of the braid of the outer layer 14.

As has been explained above, the braid of the outer layer 14 or the outer braid can lift away from the inner layer 15, because the outer layer 14 is relatively soft or more flexible than the inner layer 15 and can move in the flow. Alternatively, the braid of the outer layer 14 can have a stable structure. In particular, the braid of the outer layer 14 can have reinforcing wires, which limit the radial mobility of the braid of the braid of the outer layer 14. In this way, a stable gap forms between the outer layer 14 and the inner layer 15, and the braid of the outer layer 14 moves very little, if at all, in the blood stream. In this embodiment, the radial stability or stiffness of the outer layer 14 corresponds approximately to the radial stability or stiffness of the inner layer 15. This means that more or less the same forces are needed to widen the outer layer 14 and to widen the inner layer 15. The stable outer braid or the stable outer layer 14 is suitable in particular in connection with the above-described embodiment in which the shape of the outer layer 14 in the rest state is curved radially outward or in which the outward curvature is stamped on and the gap 16 between the outer layer 14 and the inner layer forms automatically upon release from the catheter. The automatic formation of the gap 16 means generally that the widening of the outer layer 14 is effected by internal forces or at least predominantly by internal forces of the outer layer 14. This process can be assisted by the external forces applied by the blood flow. However, in this embodiment, the widening is primarily attributable to the properties of the shape-memory material and the associated internal forces.

FIG. 23 shows another illustrative embodiment of the invention in which the braid of the outer layer 14, or generally the outer layer 14, has an undulating contour in cross section. Generally, the distance between the outer layer 14 and inner layer 15 varies, with the distance alternately increasing and decreasing. The undulating contour is particularly effective in slowing down the flow in the aneurysm 31. The undulating structure can have at least two peaks and, lying between these, a valley. In the illustrative embodiment according to FIG. 23, the undulating contour is formed with four peaks. Another number of peaks is possible. As can be seen in FIG. 23, the peaks have different heights. The height of the peaks decreases in the proximal and distal directions of the tubular body 10. The peaks are highest in the middle area of the undulating contour. The outer contour of the peaks, which is defined by their points or sections farthest away from the inner layer 15, corresponds approximately to the shape of the aneurysm that is to be treated. The outer contour (enveloping surface) of the undulating contour is adapted to the shape of the aneurysm.

At least some of the valleys can be spaced apart from the inner layer 15. It is possible for all the valleys to be spaced apart from the inner layer 15. Alternatively, at least some of the valleys can touch the inner layer 15. It is possible for all of the valleys to touch the inner layer 15.

The contact sites between the valleys and the inner layer 15 can be produced by connections between the braids of the outer layer 14 and of the inner layer 15. This applies to some of the valleys or to all of the valleys. The braid of the outer layer 14 can be connected to the braid of the inner layer 15 at a number of sites spaced apart from each other in the axial direction. This can be done, for example, by using sleeves, crimp sleeves or other connecting techniques, for example cohesively bonded connections. The sleeves can be C-shaped, for example, and can be fitted subsequently, i.e. after the interweaving to connect the two braids or the multiple braids.

Alternatively or in addition, the undulating structure can be preconditioned by heat treatment, such that the undulating structure forms in the rest state. A shape-memory material known per se, for example nitinol, is used for this. Purely mechanical shaping is possible, in which case the wave shape is stretched out in the catheter and recovers the undulating rest state after release.

A particularly important aspect of this illustrative embodiment, but one to which the invention is not limited, is that those areas that are to expand radially outward have a different braid structure than those areas of the undulating contour or of the undulating structure that form the valleys, in particular those areas that are intended to remain in contact with the braid of the inner layer 15. For example, the braiding angle in the areas that are intended to lift, particularly in the area of the peaks, can be smaller than the braiding angle of the areas that are not intended to lift, particularly in the area of the valleys. A braid that has a relatively small braiding angle can widen comparatively easily. During widening, the braiding angle increases on account of the axial compression during the widening. Those areas that are radially more stable and can therefore widen less readily have a larger braiding angle. These are the areas in which the valleys of the structure form. For example, the braiding angle can be larger than 45° in the area of the valleys and smaller than 45° in the area of the peaks.

The areas with a small braiding angle, or a smaller braiding angle than in other areas, are associated with a lower axial shortening during expansion. This means a greater radial widening with lower axial compression. This has the effect that, upon axial compression of the inner layer, the areas with the small braiding angle (peaks) have to widen outward, so that the structure shortens at the same time. The outer layer has in fact to shorten if it is connected distally to the inner layer or if the inner layer presses it outward onto the vessel wall and therefore blocks it.

Some or all of the aforementioned possibilities for forming the undulating structure can be combined with one another. For example, the undulating structure can be obtained from a combination of heat treatment (pre-embossing of the contour) and/or different braiding angles and/or mechanical connections between the inner layer 15 and outer layer 14.

In connection with the offset of the outer layer 14 relative to the inner layer 15, it is disclosed that the braids can also be offset from each other in the rest state. This means that the proximal end of one braid is offset in the axial direction to the proximal end of the other braid. In addition or alternatively, the distal braid ends of the two braids or of the multiple braids can also be offset from each other in the axial direction in the rest state. Specifically, the proximal end of the braid of the outer layer 14 and/or the distal end of the braid of the outer layer 14 can each be axially offset inward with respect to the proximal and/or distal end of the braid of the inner layer 15.

The braid of the outer layer 14 can have at least one and a half times as many wires as the braid of the inner layer 15, in particular at least twice as many wires, in particular at least three times as many wires, in particular at least 4 times as many wires, as the braid of the inner layer 15. These ranges of the wire numbers are disclosed and claimed in connection with all of the illustrative embodiments.

The undulating structure has the advantage of great axial compressibility. In this way, the braid of the outer layer 14 can be adapted well to different aneurysm lengths and widths.

The gap 16, which forms at least during use between the braid of the inner layer 15 and the braid of the outer layer 14, merges continuously, at the proximal and/or distal end of the gap 16, into the jacket surface of the tubular body 10. This is shown by way of example in FIG. 12 or in FIG. 22. The same is true in the case of treatment of a saccular aneurysm in the circumferential direction. Here too, the gap or the raised braid area of the outer layer 14 merges continuously into the jacket surface of the body 10. Things are slightly different in the treatment of a fusiform aneurysm, in which case an annular gap 16 extending in the circumferential direction forms, or is preconditioned, between the inner layer 15 and the outer layer 14. The maximum gap width, i.e. the distance between the inner layer 15 and the outer layer 14, is 50% of the expanded diameter of the tubular body. The expanded diameter relates to the free tubular body on which no external forces act, and which is therefore not arranged in the vessel. The minimum gap width is 5% of the expanded diameter of the tubular body 10. The same definition of the expanded diameter as described above applies here too. Intermediate values of the aforementioned maximum range are possible. For example, the gap width can be at most 45% of the expanded diameter, in particular at most 40%, in particular at most 35%, in particular at most 30%, in particular at most 25%, in particular at most 20%, in particular at most 15%, in particular at most 10% of the expanded diameter. The lower gap range can be at least 5%, in particular at least 10%, in particular at least 15%, in particular at least 20% of the expanded diameter of the tubular body 10. The aforementioned lower and upper limits can be combined with one another.

The device can have several plies which extend in a layered arrangement on the circumference of the body 10 and overlap one another, in particular partially overlap one another. A gap 16 is formed in each case between the individual plies. Two gaps form in the case of three plies, three gaps in the case of four plies, etc.

Particularly in the treatment of fusiform aneurysms, it is advantageous if the outer ply or the outer layer 14 lies close to the inside wall of the aneurysm or even comes into contact therewith. The lattice structure of the outer ply thus stabilizes the wall of the aneurysm and slows down the flow in the vicinity of the wall.

In addition, an intermediate ply or intermediate layer 14*a* can be provided which, during use, is spaced apart from the inner ply or the inner layer 15 and from the outer ply or the outer layer 14. The intermediate ply is arranged in the aneurysm during use. The inner ply is flush with the neck of the aneurysm. It is possible to provide several intermediate plies or intermediate layers 14*a* which protrude into the aneurysm and progressively slow down the flow. This design is particularly suitable for fusiform aneurysms, since these can be difficult to fill with coils. This affords a simple possibility of introducing material in the form of braided layers into the aneurysm.

The braided layers protruding into the aneurysm form outer layers which, as clot-forming layers, contribute to occluding the aneurysm.

The different widening or the different degree of lifting of the layers, and therefore the gap formation between the individual layers, can be achieved by different braiding angles of the layers. In addition or alternatively, the gap formation can be achieved by use of a shape-memory material, by different diameters being stamped on the layers through a suitable heat treatment known per se.

Figure 24:
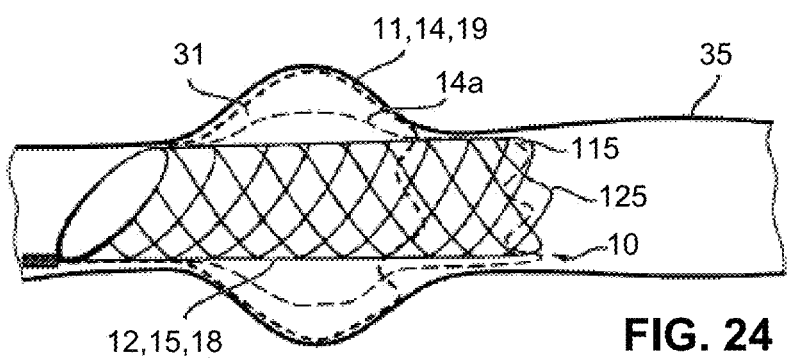
FIG. 24 shows a perspective side view of a medical device in another illustrative embodiment according to the invention that is used to treat a fusiform aneurysm.

In the example according to FIG. 24, the outer layer 14 is at least partially in contact with the aneurysm wall. The distal end of the outer layer 14 is located in the aneurysm or at least at the end of the aneurysm neck. The advantage of this configuration, in which the outer layer 14 does not extend past the aneurysm neck into the vessel, is that the distal end of the outer layer 14 can freely expand and the entire outer layer can bear safely on the wall of the aneurysm. Structurally, this is achieved by the fact that the outer layer 14 is axially shorter than the body 10 and/or an optional intermediate layer 14*a*. The outer layer 14 can be shorter than the body 10 by at least 10%, in particular at least 20%, in particular at least 30%, in particular at least 40%, in particular at least 50%, in particular at least 60%, in particular at least 70%.

The distal end of the outer ply or of the outer layer 14 can alternatively extend, like the middle ply, distally beyond the aneurysm neck. Here, the ply is pressed by the inner braid or the inner layer 15 against the vessel wall and thus fixed. When the distal end is fixed by the inner ply or inner layer 15, the expansion of the outer ply or outer layer 14 into the aneurysm is determined to a greater degree by the braiding angle.

Therefore, if a defined gap 16 is to be set, the distal end and proximal end must be blocked. For this purpose, a suitably long outer layer 14 is provided. If the expansion is to be free, in order to bear against the wall, the length of the outer layer 14 must be chosen such that there is no blocking of the outer layer 14.

Generally, only the proximal ends of the plies or layers 14, 14*a*, 15 are interconnected. The blocking of the distal ends, if desired, is obtained by friction during use. This design is a technically simple one. The braid distorts only slightly. If the blocking at the distal end is obtained by friction, the braids can shift relative to one another during the positioning, specifically at the distal end, which reduces the danger of distortion and promotes adaptation to the anatomy.

By contrast, if the distal end of the layers is connected, secure blocking is achieved and the gap formation can be controlled with precision by the different braiding angles.

These observations also relate to the case where the body 10 is composed of only 2 plies, namely the inner layer 15 and the outer layer 14, or of more than 2 or 3 plies, etc.

LIST OF REFERENCE SIGNS

10 tubular body
11 first lattice structure
12 second lattice structure
13 third lattice structure
14 outer layer
14*a* intermediate layer
15 inner layer
16 gap
17 connecting sleeve
18 carrier
19 net
20 delivery system
21 coil catheter
30 blood vessel
31 aneurysm
32 aneurysm neck
34 aneurysm wall
35 vessel wall
36 attack region
40 conventional aneurysm stent
41 first wire
42 second wire
43 end strand of the first lattice structure 11
44 end strand of the second lattice structure 12
45 anchoring sites
46 terminal edge
110 proximal end of the first lattice structure 11
111 middle section
112 wire of the first lattice structure 11
113 transition section
115 distal end of the first lattice structure 11
116 edge section
120 proximal end of the second lattice structure 12
122 wire of the second lattice structure 12
125 distal end of the second lattice structure 12
130 proximal end of the third lattice structure 13
135 distal end of the third lattice structure 13
$F_G$ vessel flow
$F_W$ eddy flow
$F_D$ through-flow
B bulge E elongation of the blood vessel 30
K shortening of the transition section 113
P pressure
W widening of the blood vessel 30
R narrowing

What is claimed is:

1. A stent for treating an aneurysm, the stent comprising:
a first lattice structure having a first end and a second end, and a second lattice structure having a third end and a fourth end, the first lattice structure and the second lattice structure defining in combination with each other a single device body having a compressed state and an expanded state, the first lattice structure forming an inner layer of the device body, and the second lattice structure forming an outer layer of the device body overlapping the inner layer,
the device body comprising a first wall section being substantially tubular in the expanded state,
the first lattice structure being disposed substantially coaxially with the second lattice structure,
the first lattice structure comprising a first plurality of wires, the first plurality of wires comprising nitinol and being interwoven to form a first closed mesh of the first lattice structure, each of the first plurality of wires having a first diameter, and
the second lattice structure comprising a second plurality of wires, the second plurality of wires comprising nitinol and being interwoven to form a second closed mesh of the second lattice structure, a size of each cell of the second closed mesh being different from a size of each cell of the first closed mesh, each of the second plurality of wires having a second diameter different than the first diameter,
the first lattice structure and the second lattice structure being configured to be positioned within an arterial blood vessel having a cross-sectional diameter in a range between 2 mm and 6 mm; and
a plurality of punctiform connections connecting the first lattice structure and the second lattice structure, the plurality of punctiform connections being distributed axially along the device body and obliquely with respect to a longitudinal axis of the device body, each of the plurality of punctiform connections being axially offset from the first and second ends of the first lattice structure and from the third and fourth ends of the second lattice structure, the plurality of punctiform connections permitting movement of the lattice structures relative to each other in areas of the device body between adjacent punctiform connections, permitting radial movement of a portion of the first end and an overlapping portion of the third end relative to each other, and permitting radial movement of a portion of the second end and an overlapping portion of the fourth end relative to each other, the plurality of punctiform connections preventing complete displacement of the first and second lattice structures relative to each other, wherein the plurality of punctiform connections are formed by a wire wrapping around the outside of the second lattice structure and the first lattice structure,
wherein the plurality of punctiform connections permit movement, at each of the plurality of punctiform connections, of at least one wire of the first plurality of wires of the first lattice structure relative to at least one wire of the second plurality of wires of the second lattice structure such that the at least one wire of the first plurality of wires of the first lattice structure slides on the at least one wire of the second plurality of wires of the second lattice structure at each of the plurality of punctiform connections,
wherein a quantity of the second plurality of wires comprises no more than 32 wires and is different than a quantity of the first plurality of wires, and
wherein each of the second plurality of wires has a cross-sectional diameter of at least 40 μm.

2. The stent of claim 1, wherein the at least one wire of the first plurality of wires of the first lattice structure and the at least one wire of the second plurality of wires of the second lattice structure are arranged loosely alongside each other at each of the plurality of punctiform connections.

3. The stent of claim 1, wherein the at least one wire of the first plurality of wires of the first lattice structure and the at least one wire of the second plurality of wires of the second lattice structure form the plurality of punctiform connections.

4. The stent of claim 1, wherein each of the plurality of punctiform connections is limited to at most 2 mesh cells of the first closed mesh or to at most 2 mesh cells of the second closed mesh.

5. The stent of claim 1, wherein each of the plurality of punctiform connections is surrounded on at least two sides by the first lattice structure or is surrounded on at least two sides by the second lattice structure.

6. The stent of claim 1, wherein the first plurality of wires has a first braiding angle and the second plurality of wires has a second braiding angle, the first braiding angle being different than the second braiding angle.

7. The stent of claim 1, wherein each of the plurality of punctiform connections comprises a linear extent or an areal extent.

8. The stent of claim 7, wherein the first lattice structure and the second lattice structure immediately adjacent to the linear extent or the areal extent move relative to each other.

9. The stent of claim 1, wherein the first lattice structure and the second lattice structure in the areas of the device body between adjacent punctiform connections are movable relatively to each other in an axial direction of the device body.

10. The stent of claim 1, wherein the wire wrapping around the outside of the second lattice structure is separate from the first plurality of wires of the first lattice structure and separate from the second plurality of wires of the second lattice structure.

11. The stent of claim 1, wherein the wire wrapping around the outside of the second lattice structure is one of the first plurality of wires of the first lattice structure.

12. A system treating an aneurysm, comprising:
a stent comprising:
a first lattice structure having a first end and a second end, and a second lattice structure having a third end and a fourth end, the first lattice structure and the second lattice structure defining in combination with each other a single device body having a compressed state and an expanded state, the first lattice structure forming an inner layer of the device body, and the second lattice structure forming an outer layer of the device body overlapping the inner layer,
the device body comprising a first wall section being substantially tubular in the expanded state,
the first lattice structure being disposed substantially coaxially with the second lattice structure,
the first lattice structure comprising a first plurality of wires, the first plurality of wires comprising nitinol and being interwoven to form a first closed mesh of the first lattice structure, each of the first plurality of wires having a first diameter, and
the second lattice structure comprising a second plurality of wires, the second plurality of wires comprising nitinol and being interwoven to form a second closed mesh of the second lattice structure, a size of each cell of the second closed mesh being different from a size of each cell of the first closed mesh, each of the second plurality of wires having a second diameter different than the first diameter, the first lattice structure and the second lattice structure being configured to be positioned within an arterial blood vessel having a cross-sectional diameter in a range between 2 mm and 6 mm; and a plurality of punctiform connections connecting the first lattice structure and the second lattice structure, the plurality of punctiform connections being distributed axially along the device body and obliquely with respect to a longitudinal axis of the device body, each of the plurality of punctiform connections being axially offset from the first and second ends of the first lattice structure and from the third and fourth ends of the second lattice structure, the plurality of punctiform connections permitting movement of the lattice structures relative to each other in areas of the device body between adjacent punctiform connections, permitting radial movement of a portion of the first end and an overlapping portion of the third end relative to each other, and permitting radial movement of a portion of the second end and an overlapping portion of the fourth end relative to each other, the plurality of punctiform connections preventing complete displacement of the first and second lattice structures relative to each other, wherein the plurality of punctiform connections are formed by a wire wrapping around the outside of the second lattice structure and the first lattice structure, wherein the plurality of punctiform connections permit movement, at each of the plurality of punctiform connections, of at least one wire of the first plurality of wires of the first lattice structure relative to at least one wire of the second plurality of wires of the second lattice structure such that the at least one wire of the first plurality of wires of the first lattice structure slides on the at least one wire of the second plurality of wires of the second lattice structure at each of the plurality of punctiform connections, wherein a quantity of the second plurality of wires comprises no more than 32 wires and is different than a quantity of the first plurality of wires, and wherein each of the second plurality of wires has a cross-sectional diameter of at least 40 μm; and a delivery system comprising a flexible supply device configured to be coupled to the stent.

13. A stent for treating an aneurysm, the stent comprising:

a first lattice structure having a first end and a second end, and a second lattice structure having a third end and a fourth end, the first lattice structure and the second lattice structure defining in combination with each other a single device body having a compressed state and an expanded state, the first lattice structure forming an inner layer of the device body, and the second lattice structure forming an outer layer of the device body overlapping the inner layer, the device body comprising a first wall section being substantially tubular in the expanded state, the first lattice structure being disposed substantially coaxially with the second lattice structure, the first lattice structure comprising a first plurality of wires, the first plurality of wires comprising nitinol and being interwoven to form a first closed mesh of the first lattice structure, each of the first plurality of wires having a first diameter, and the second lattice structure comprising a second plurality of wires, the second plurality of wires comprising nitinol and being interwoven to form a second closed mesh of the second lattice structure, a size of each cell of the second closed mesh being different from a size of each cell of the first closed mesh, each of the second plurality of wires having a second diameter different than the first diameter, the first lattice structure and the second lattice structure being configured to be positioned within an arterial blood vessel; and a plurality of punctiform connections connecting the first lattice structure and the second lattice structure, the plurality of punctiform connections being distributed axially along the device body and obliquely with respect to a longitudinal axis of the device body, each of the plurality of punctiform connections being axially offset from the first and second ends of the first lattice structure and from the third and fourth ends of the second lattice structure, the plurality of punctiform connections permitting movement of the lattice structures relative to each other in areas of the device body between adjacent punctiform connections, permitting radial movement of a portion of the first end and an overlapping portion of the third end relative to each other, and permitting radial movement of a portion of the second end and an overlapping portion of the fourth end relative to each other, the plurality of punctiform connections preventing complete displacement of the first and second lattice structures relative to each other, wherein the plurality of punctiform connections are formed by a wire wrapping around the outside of the second lattice structure and the first lattice structure, wherein the plurality of punctiform connections permit movement, at each of the plurality of punctiform connections, of at least one wire of the first plurality of wires of the first lattice structure relative to the at least one wire of the second plurality of wires of the second lattice structure, such that the at least one wire of the first plurality of wires of the first lattice structure slides on the at least one wire of the second plurality of wires of the second lattice structure at each of the plurality of punctiform connections, wherein a quantity of the second plurality of wires comprises no more than 32 wires and is different than a quantity of the first plurality of wires, and wherein each of the second plurality of wires has a cross-sectional diameter of at least 40 μm.

14. The stent of claim 13, wherein a portion of the first lattice structure and a portion of the second lattice structure immediately adjacent a respective punctiform connection move relative to each other in an axial direction of the device body.

15. The stent of claim 13, wherein each of the plurality of punctiform connections is limited to at most 4 mesh cells of the closed mesh of the first lattice structure or to at most 4 mesh cells of the closed mesh of the second lattice structure.

16. The stent of claim 13, wherein 4 or fewer mesh cells of the second lattice structure are connected to at least 4 mesh cells of the first lattice structure.

17. The stent of claim 13, wherein each of the plurality of punctiform connections is limited to at most 2 mesh cells of the closed mesh of the first lattice structure or to at most 2 mesh cells of the closed mesh of the second lattice structure.

18. The stent of claim 17, wherein each of the plurality of punctiform connections is surrounded on at least two sides by the first lattice structure or is surrounded on at least two sides by the second lattice structure.

19. The stent of claim 18, wherein the first plurality of wires has a first braiding angle and the second plurality of wires has a second braiding angle, the first braiding angle being different than the second braiding angle.

20. The stent of claim 13, wherein each of the plurality of punctiform connections comprises a linear extent or an areal extent.

21. The stent of claim 13, wherein the wire wrapping around the outside of the second lattice structure is separate from the first plurality of wires of the first lattice structure and separate from the second plurality of wires of the second lattice structure.

22. The stent of claim 13, wherein the wire wrapping around the outside of the second lattice structure is one of the first plurality of wires of the first lattice structure.

23. The system of claim 12, wherein the wire wrapping around the outside of the second lattice structure is one of the first plurality of wires of the first lattice structure.

24. The system of claim 23, wherein the wire wrapping around the outside of the second lattice structure is separate from the first plurality of wires of the first lattice structure and separate from the second plurality of wires of the second lattice structure.

* * * * *

UNITED STATES PATENT AND TRADEMARK OFFICE
CERTIFICATE OF CORRECTION

PATENT NO. : 10,709,588 B2  
APPLICATION NO. : 15/351746  
DATED : July 14, 2020  
INVENTOR(S) : Cattaneo et al.

Page 1 of 1

It is certified that error appears in the above-identified patent and that said Letters Patent is hereby corrected as shown below:

In the Claims

In Column 38, Claim 12, Line 44, delete "system treating" and insert --system for treating--.

In Column 40, Claim 13, Line 38, delete "to the at" and insert --to at--.

In Column 40, Claim 13, Line 40, delete "structure," and insert --structure--.

Signed and Sealed this  
Twenty-ninth Day of September, 2020

Andrei Iancu  
*Director of the United States Patent and Trademark Office*